United States Patent [19]

Hu et al.

[11] Patent Number: 5,328,828
[45] Date of Patent: Jul. 12, 1994

[54] COMPOSITIONS AND METHODS FOR DETERMINING THE PRESENCE OF AMPHETAMINES IN A SAMPLE SUSPECTED OF CONTAINING AMPHETAMINE AND/OR METHAMPHETAMINE

[75] Inventors: Mae W. Hu, Los Altos Hills; Cheng-I Lin, San Jose, both of Calif.; Chen-jung Hsu, Elkhart, Ind.; James V. Freeman, San Jose, Calif.; Marcel Pirio, San Jose, Calif.; Edwin F. Ullman, Atherton, Calif.

[73] Assignee: Syntex (U.S.A.) Inc., Palo Alto, Calif.

[21] Appl. No.: 916,568

[22] Filed: Jul. 20, 1992

Related U.S. Application Data

[62] Division of Ser. No. 290,487, Dec. 23, 1988, Pat. No. 5,135,863.

[51] Int. Cl.$^5$ ............... G01N 33/536; G01N 33/537; G01N 33/542
[52] U.S. Cl. .................... 435/7.9; 435/7.92; 436/536; 436/537; 436/538; 436/548; 436/816; 436/822
[58] Field of Search ............... 435/7.9, 7.92; 436/536, 436/537, 538, 815, 816, 822, 548

[56] References Cited

U.S. PATENT DOCUMENTS

| | | | |
|---|---|---|---|
| 3,646,346 | 2/1972 | Catt | 250/83 |
| 3,654,090 | 4/1972 | Schuurs et al. | 195/103.5 |
| 3,791,932 | 2/1974 | Schuurs et al. | 195/103.5 R |
| 3,817,837 | 6/1974 | Rubenstein et al. | 195/103.5 R |
| 3,878,187 | 4/1975 | Schneider et al. | 260/121 |
| 3,996,344 | 12/1976 | Gross | 424/1.5 |
| 3,996,345 | 12/1976 | Ullman et al. | 424/12 |
| 4,016,146 | 4/1977 | Soares | 260/112 R |
| 4,041,076 | 8/1977 | Avenia et al. | 260/559 A |
| 4,062,733 | 12/1977 | Edwards et al. | 195/103.7 |
| 4,067,774 | 1/1978 | Rubenstein et al. | 195/63 |
| 4,067,959 | 1/1978 | Bolz | 424/1 |
| 4,160,645 | 7/1979 | Ullman | 23/230 B |
| 4,329,281 | 5/1982 | Christenson et al. | 260/112 B |
| 4,868,132 | 9/1989 | Byrnes et al. | 436/546 |
| 5,262,333 | 11/1993 | Heiman et al. | 436/537 |

FOREIGN PATENT DOCUMENTS 89313439 4/2491 European Pat. Off. .

Primary Examiner—David Saunders
Attorney, Agent, or Firm—Theodore J. Leitereg; Janet K. Kaku

[57] ABSTRACT

The instant invention is directed toward an immunoassay which can determine the presence of amphetamines in a sample suspected of containing amphetamine and/or methamphetamine by employing at least two conjugates, each comprised of a functionally similar label bound to an amphetamine analog and a methamphetamine analog respectively and an antibody to amphetamine and an antibody to methamphetamine wherein at least one of the antibodies is a monoclonal antibody.

12 Claims, 3 Drawing Sheets

COMPOSITIONS AND METHODS FOR DETERMINING THE PRESENCE OF AMPHETAMINES IN A SAMPLE SUSPECTED OF CONTAINING AMPHETAMINE AND/OR METHAMPHETAMINE

This is a divisional of pending application Ser. No. 07/290,487, filed Dec. 23, 1988, and now U.S. Pat. No. 5,135,863.

BACKGROUND OF THE INVENTION

1. Field of the Invention

This invention relates to immunoassay compositions and methods for determining the presence of amphetamines in a sample suspected of containing amphetamine and/or methamphetamine. In particular, the immunoassay compositions of this invention for determining the presence amphetamines in a sample suspected of containing amphetamine and/or methamphetamine are comprised of two conjugates containing functionally similar labels, one bound to an amphetamine ligand analog and the other bound to a methamphetamine ligand analog. These immunoassay compositions may also include an antibody to amphetamine and an antibody to methamphetamine wherein at least one of the antibodies is a monoclonal antibody. The compositions of this invention are particularly useful for assaying for amphetamines even in the case where the monoclonal antibody is moderately cross-reactive with the conjugate which is bound more strongly by the other antibody.

2. Related Art

A wide variety of patents and literature references disclose different immunoassay techniques. The following list is merely illustrative of some of these techniques which can find application in this invention. The following is a list of Unites States patents and a general statement of the type of label involved:

U.S. Pat. Nos. 3,646,346, Radioactive Label; 3,654,090, 3,791,932 and 3,817,837, (Rubonstein) et al.) Enzyme Labels; 3,996,345; Flurorescer-Quencher Labels; 4,062,733, Radioactive Label; 4,067,959, Fluorescer or Enzyme Labels; and 4,160,645, Non-Enzymatic Catalyst Label.

Typically, these immunoassays will employ an antibody whose structure will recognize (have a binding affinity for) the analyte specific for that antibody. The immunoassay is conducted with a signal producing system which produces a detectible change in signal upon binding of the analyte to the antibody. Accordingly, when testing for an analyte in a sample, a detectible change in signal from that produced with a negative sample or calibrator is taken as a positive result for the presence of that analyte in the sample.

However, there is a problem when such techniques are employed to assay for amphetamines in a sample suspected of containing amphetamine and/or methamphetamine. The problem arises because these assays employ a single antiserum or antibody which can recognize both amphetamine and methamphetamine. In order for this antibody to recognize both amphetamine and methamphetamine, it is necessary for it (a) to be capable of recognizing a particular spatial and polar organization common to amphetamine and methamphetamine; and (b) to lack specific recognition of those structural features of amphetamine and methamphetamine that are different. Because such an antibody recognizes structural features that are common to both of these compounds but lacks specific recognition of the structural features that are different, it is able to recognize both compounds and the assay will produce a positive result for a sample containing amphetamine and/or methamphetamine. However, all antibodies that recognize both compounds have been found to recognize molecules other than amphetamine and methamphetamine that share some but not all of the common spatial and polar features of amphetamine and methamphetamine. Such antibodies may produce false positive results in the assay of certain samples, i.e., a positive result for amphetamines in the absence of amphetamine and methamphetamine. In point of fact, commercial immunoassays for amphetamines which utilize a single antibody either are sensitive to only amphetamine or methamphetamine or recognize certain prescription and OTC drugs and normal metabolic products which are structurally similar to amphetamine and methamphetamine including drugs such as phenylpropanolamine, pseudoephedrine, phentermine, mephentermine, etc., and the metobolic product tyramine. As a result, test samples containing one or more of these drugs or metabolic products can produce false positives for amphetamines.

This problem of false positives arising from testing for amphetamines using a single antibody is particularly troublesome because in actual practice, every positive test result requires a follow-up test to confirm the presence of amphetamines. Such follow-up tests inherently add additional laboratory time and expense to the immunoassay particularly if a substantial portion of these positive results are false positives. Although in principle separate tests could be run each using an antibody specific for one drug, this too increases the number of tests that must be run. Accordingly, it would be particularly desirable to develop an immunoassay which could test for amphetamines while at the same time result in substantially reduced occurrences of false positives arising from compounds which are structurally related to amphetamines.

This would not be a difficult problem if antibodies could be prepared that were completely specific for amphetamine and would not bind to a ligand analog of methamphetamine that was bound to a detectible label, and antibodies specific for methamphetamine were available that would not bind to a ligand analog of amphetamine that was bound to a detectible label. If such antibodies could be made, the components of two specific assays could be combined to provide a single assay for amphetamines. However, such antibodies are not available and the binding of one antibody to the label conjugate of a ligand analog of the other drug might be expected to prevent the construction of a useful assay.

What we have found and what the instant invention is directed toward is an immunoassay composition which can assay for the presence of amphetamines in a sample suspected of containing amphetamine and/or methamphetamine while producing substantially fewer false positives wherein two antibodies are used together with conjugates of a ligand analog of each of the drugs with a label.

U.S. Pat. No. 4,329,281 discloses 4-[4-[2-(aminopropyl)]phenyl]butanoic acid and its N-methyl derivative as useful in preparing immunogens which can be respectively employed in the elicitation of polyclonal antibodies selective to amphetamine and methamphetamine. These antibodies are then used in immunoassays.

U.S. Pat. No. 4,041,076 discloses amphetamine and methamphetamine derivatives substituted at the para phenyl position with —O(CH$_2$)$_n$CO$_2$H wherein n is 1 to 3. These derivatives are useful in preparing immunogens which can be employed to elicit polyclonal antibodies selective to amphetamine and methamphetamine. These antibodies are then used in immunoassays.

U.S. Pat. No. 4,067,774 discloses amphetamines bound to enzymes via a —OZC(O)— group on the phenyl ring wherein Z is hydrocarbylene of from 1 to 7 carbon atoms. These enzyme linked compounds are used in immunoassays.

U.S. Pat. Nos. 3,996,344 and 4,016,146 discloses the preparation of amphetamine and methamphetamine analogs which are useful in preparing immunogens which can be employed to elicit polyclonal antibodies selective to amphetamine and methamphetamine. The compounds so disclosed are substituted on the phenyl group with HOOCCH$_2$CH$_2$C(O)—.

Lastly, N-carboxymethyl amphetamine has been employed in preparing immunogens which can be employed to elicit a polyclonal antibody which recognizes amphetamine and methamphetamine.

SUMMARY OF THE INVENTION

In one of its composition aspects, the instant invention is directed to a composition which comprises two conjugates, each containing functionally similar labels, wherein one label is bound to an amphetamine ligand analog and the other label is bound to a methamphetamine ligand analog. In another composition aspect, the instant invention is directed to a composition for the assay of amphetamines in a sample suspected of containing amphetamine and/or methamphetamine which comprises an aqueous solution containing in addition to these conjugates, an antibody to amphetamine and an antibody to methamphetamine wherein at least one of said antibodies is a monoclonal antibody.

Preferably, this composition contains a monoclonal antibody to amphetamine and a monoclonal antibody to methamphetamine.

When employed in an immunoassay, this composition may additionally contain any other necessary components of a signal producing system needed to produce a detectible signal wherein the amount of signal is related to the amount of amphetamines in the sample.

The immunoassay composition of this invention is particularly useful in assaying for amphetamines while producing substantially fewer false positives than immunoassays which employ a single antibody which recognizes both amphetamine and methamphetamine. Additionally, the composition can be used to assay for amphetamines even in the case where the monoclonal antibody is moderately cross-reactive (as later defined) with that conjugate which can bind more strongly to the other antibody.

In its method aspect, one embodiment of the instant invention is directed to a method for the assay of amphetamines in a sample suspected of containing amphetamine and/or methamphetamine which comprises (A) combining in an aqueous medium (a) the sample; (b) an antibody to amphetamine and an antibody to methamphetamine wherein at least one of the antibodies is a monoclonal antibody; and (c) two conjugates, each containing a label that is functionally similar to the other wherein one label is conjugated to a ligand analog of amphetamine and the other label is conjugated to a ligand analog of methamphetamine under conditions allowing the antibodies to bind to the conjugates;

(B) with or without separating either the bound or unbound conjugates from the medium obtained from step A, contacting the conjugates obtained from step A with any necessary components of the signal producing system wherein a signal is produced that is related to the presence of amphetamines in the sample; and (C) determining the signal.

Another aspect of the instant invention involves a kit for use in the assay. Such a kit comprises the following components:

(a) an antibody to amphetamine and an antibody to methamphetamine wherein at least one of said antibodies is monoclonal;

(b) two conjugates, each containing a label that is functionally similiar to the other wherein one is bound to an amphetamine ligand analog and the other is bound to a methamphetamine ligand analog.

The compositions of this invention employ antibodies and conjugates of ligand analogs with labels for use in an amphetamine/methamphetamine assay. Accordingly, in this regard, the instant invention is directed to certain compounds which can be used in the assay or are precursors to compounds which can be used. Therefore, in its compound aspect, one embodiment of the instant invention is directed toward a compound of the formula:

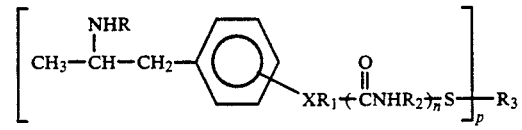

wherein:
R is hydrogen or methyl;
X is oxygen, sulfur or is a bond;
R$_1$ is alkylene of 1 to 6 carbon atoms;
R$_2$ is alkylene of 2 to 6 carbon atoms;
n is 0 or 1;
R$_3$ is hydrogen, —SR$_4$ wherein R$_4$ is alkyl of from 1 to 6 carbon atoms, or is (A)$_p$Z wherein A is derived from a functionality capable of reacting with a thiol group to form a bond between the sulfur atom of the thiol group and A, and Z is a poly(amino acid);
p is 1 when R$_3$ is hydrogen or —SR$_4$ and is a number from 1 to the molecular weight of the poly(amino acid) divided by 500 when R$_3$ is (A)$_p$Z and with the proviso that when n is zero then R$_1$ is alkylene of 2 to 6 carbon atoms and with the further proviso that the benzene ring is bonded to X at the position meta or para to the

group and when X is a bond, the benzene ring is bonded to X at the para position.

DETAILED DESCRIPTION OF THE INVENTION

Figure 1A:
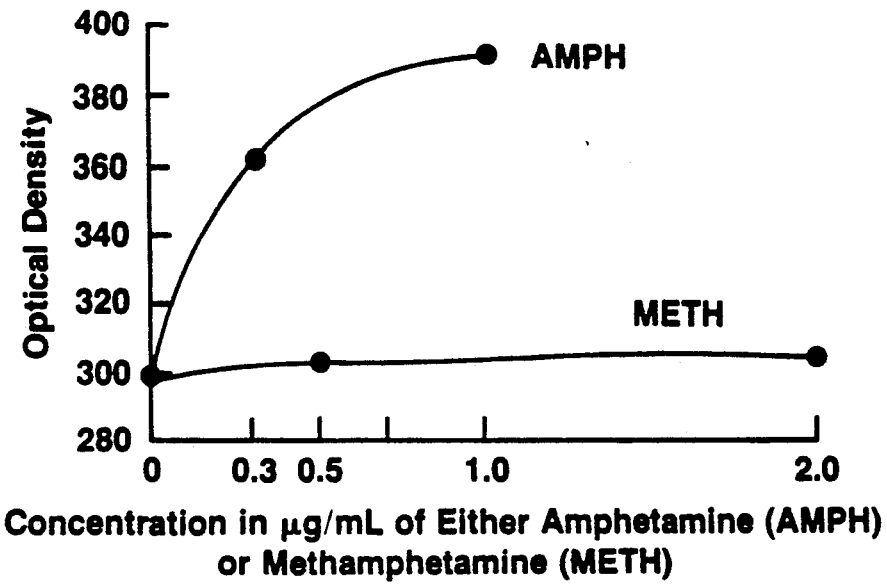
FIG. 1a and FIG. 1b graphically depict the assay responses to amphetamine and methamphetamine in assays utilizing a monoclonal antibody for amphetamine where the assay of FIG. 1a further utilizes a conjugate of an amphetamine ligand analog with glucose-6-phosphate dehydrogenase and the assay of FIG. 1b further utilizes a conjugate of a methamphetamine ligand analog with glucose-6-phospate dehydrogenase.

An immunoassay composition is provided which is useful for assaying for the presence of amphetamines in a sample suspected of containing amphetamine and/or methamphetamine while producing substantially reduced levels of false positives.

The assay composition of this invention is useful in a wide variety of previously employed immunoassay methods, both homogeneous and heterogeneous. The conditions under which these immunoassays have been carried out will normally be applicable with the subject composition. Thus, the compositions of this invention can be used in prior art immunoassays so as to provide a means to determine the presence of amphetamines in a sample suspected of containing amphetamine and/or methamphetamine. By appropriate choice of components for producing a detectible signal, the detectible signal may be observed visually or by means of various apparatus, i.e., detection means, such as spectrophotometers, fluorometers, scintillation counters, etc.

In the assay composition, there are employed two or more reagents which will comprise the signal producing system. Key reagents in the signal producing system are two conjugates each containing a label conjugated to a ligand analog. The choice of protocol will determine whether an increase or decrease in the amount of signal generated by the signal producing system determines the amount of amphetamines in the assay sample.

Before proceeding further with the description of the specific embodiments of the present invention, a number of terms will be defined.

Amphetamines—the drugs amphetamine and methamphetamine.

Analyte—the amphetamines to be measured. The analytes (amphetamines) are ligands and are members of separate specific binding pairs (sbp) consisting of the ligand and an antibody for the ligand.

Ligand analog—a modified ligand which when bound to another molecule can compete with the analogous ligand or analyte for binding to an antibody, the modification providing means to join a ligand analog to another molecule. The ligand analog will usually differ from the ligand by more than replacement of a hydrogen with a bond which links the ligand analog to a hub or label, but need not. Included within the term ligand analogs are poly(ligand analogs) which are a plurality of ligand analogs joined together covalently, normally to a hub nucleus. The hub nucleus is a polyfunctional material, normally polymeric, usually having a plurality of functional groups, e.g., hydroxyl, carboxyl, amino, mercapto, ethylenic, etc. as sites for linking. The hub nucleus may be water soluble or insoluble, preferably water soluble, and will normally be at least about 30,000 molecular weight and may be 10 million or more molecular weight. Illustrative hub nuclei include polysaccharides, polypeptides (including proteins), nucleic acids, anion exchange resins, and the like. Water insoluble hub nuclei can include walls of containers, e.g. glass or plastic, glass beads, addition and condensation polymers, Sephadex and Agarose beads and the like.

Member of a specific binding pair ("sbp member")—one or two different molecules, having an area on the surface or in a cavity which specifically binds to and is thereby defined as complementary with a particular spatial and polar organization of the other molecule. The members of the specific binding pair are referred to as ligand and receptor. These will usually be members of an immunological pair such as antigen-antibody.

Ligand—any organic compound for which a receptor naturally exists or can be prepared. When the receptor is an antibody, the ligand is called an antigen.

Antibody—an immunoglobulin, or derivative or fragment thereof, having an area on the surface or in a cavity which specifically binds to and is thereby defined as complementary with a particular spatial and polar organization of another molecule. The antibody can be monoclonal or polyclonal and can be prepared by techniques that are well known in the art such as, for example, immunization of a host and collection of sera or hybrid cell line technology.

Antibody for amphetamine—a monoclonal or polyclonal antibody which is highly specific for amphetamine and has minimal recognition of methamphetamine. The antibody for amphetamine is capable of recognizing amphetamine and conjugates of an amphetamine ligand analog with a label.

Antibody for methamphetamine—a monoclonal or polyclonal antibody which is highly specific for methamphetamine and has minimal recognition of amphetamine. The antibody for methamphetamine is capable of recognizing methamphetamine and conjugates of a methamphetamine ligand analog with a label.

Minimal recognition—the binding constant for an antibody binding to a non-complementary antigen, i.e., the binding constant for amphetamine binding to the antibody for methamphetamine or the binding constant for methamphetamine binding to the antibody for amphetamine, is less than 20% and frequently less than 10% of the binding constant of the antibody for its complementary antigen.

Label—a member of the signal producing system that is conjugated to the ligand or an antibody. The label can be isotopic or non-isotopic, usually non-isotopic, including catalysts such as an enzyme, a chromogen such as a fluorescer, dye or chemiluminescers, a radioactive substance, a particle, and so forth. Identical or functionally similar labels will be conjugated, that is bound covalently or non-covalently, to amphetamine and methamphetamine or ligand analogs thereof. Functionally similar labels are labels that provide signals that are substantially identical except in intensity such as the same or closely similar derivatives of an enzyme, a fluorophore, etc.

Cross-reactivity—the ratio of the binding constant of an antibody and a ligand to the binding constant of the same antibody to its homologous ligand or antigen. When the homologous ligand is an analyte, a cross-reactive ligand will produce a signal in an assay corresponding to its cross-reactivity with the antibody.

Moderately cross-reactive—An antibody that preferentially binds a first conjugate of one ligand analog and a label is said to be moderately cross-reactive with a second conjugate of a different ligand analog and a label and the second conjugate is said to be moderately cross-reactive with the antibody when the binding constant to the second conjugate ranges from about 20% to about 80% of the binding constant to the first conjugate; that is, it has a cross-reactivity of from about 20% to about 80%.

Signal producing means—means capable of interacting with the label to produce a detectable signal. Such means include, for example, electromagnetic radiation, heat, chemical reagents, and the like. The chemical reagents can include substrates, coenzymes, enhancers, second enzymes, activators, cofactors, inhibitors, scavengers, metal ions, specific binding substances required for binding of signal generating substances, and the like.

Signal Producing System—The signal producing system may have two or more components, at least two components being conjugates containing functionally similar labels. The signal producing system generates a signal that in the presence of all of the assay components is a function of the presence or amount of amphetamines in a sample. The signal producing system includes all of the reagents required to produce a measurable signal. At least two members of the signal producing system are bound to the ligands or antibodies, usually ligands. Other components of the signal producing system can include substrates, enhancers, activators, chemiluminescent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like. The signal producing system provides a signal detectable by external means, preferably by electromagnetic radiation, usually photometrically, such as absorbance or fluorescence polarization, or by the degree of aggregation of particles, desirably by visual examination. For the most part, the other components of the signal producing system will involve a chromophoric substrate, an enzyme and ancillary reagents required for enzyme activity, where chromophoric substrates are enzymatically converted to dyes which absorb light in the ultraviolet or visible region, phosphors, fluorescers or chemiluminescers.

The signal producing system can include at least one catalyst, usually an enzyme, and at least one substrate and may include two or more catalysts and a plurality of substrates, and may include a combination of enzymes, where the substrate of one enzyme is the product of the other enzyme. The operation of the signal producing system is to produce a product which provides a detectable signal related to the amount of analyte in the sample.

A large number of enzymes and co-enzymes useful in a signal producing system are indicated in U.S. Pat. No. 4,275,149, columns 19 to 23, and U.S. Pat. No. 4,318,980, columns 10 to 14, which disclosures are incorporated herein by reference. A number of enzyme combinations are set forth in U.S. Pat. No. 4,275,149, columns 23 to 28, which combinations can find use in the subject invention. This disclosure is incorporated herein by reference.

Of particular interest are redox enzymes particularly dehydrogenases such as glucose-6-phosphate dehydrogenase, lactate dehydrogenase, etc and enzymes which involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme which employs the hydrogen peroxide to oxidize a dye precursor, that is, a peroxidase such as horse radish peroxidase, lactoperoxidase, or microperoxidase. Additional enzyme combinations may be found in the subject matter incorporated by reference. When a single enzyme is used as a label, other enzymes may find use such as hydrolases, transferases, and oxidoreductases, preferably hydrolases such as alkaline phosphatase and beta-galactosidase. Alternatively, luciferases may be used such as firefly luciferase and bacterial luciferase.

Illustrative co-enzymes which find use include NAD[H]; NADP[H]; pyridoxal phosphate; FAD[H]; FMN[H]; etc., usually coenzymes involving cycling reactions, see particularly U.S. Pat. No. 4,318,980.

The product of the enzyme reaction will usually be a dye or fluorescer. A large number of illustrative fluorescers are indicated in U.S. Pat. No. 4,275,149, columns 30 and 31, which disclosure is incorporated herein by reference.

The signal producing system may alternatively involve a fluorescent or chemiluminescent label. Fluorescent labels of particular utility are fluorescein and rhodamine derivatives, umbelliferones, phycobiliproteins and the like. Chemiluminescent labels include acridinium esters, luminol, oxalate esters, etc.

Any necessary components of the signal producing system—In addition to the label, those components, if any, which are necessary in producing a detectable signal. In some immunoassays, no additional components are necessary. For example, in some radioimmunoassays (RIA), the signal producing system employs an isotope and additional components such as a scintillation fluid may not be necessary. Similarly, in fluorescence immunoassays, the signal producing system employs a fluorescent molecule and additional components such as enhancers, quenchers and energy acceptors are frequently unnecessary. However, if the label is an enzyme, then additional components such as substrates, enhancers, activators, coenzymes, cofactors, inhibitors, scavengers, etc. may be necessary for the production of the detectable signal in this signal producing system. The necessary components for a particular signal producing system are well known in the art.

Ancillary Materials—Various ancillary materials will frequently be employed in the assay method performed in accordance with the present invention. For example, buffers will normally be present in the assay medium, as well as stabilizers for the assay medium and the assay components. Frequently, in addition to these additives, additional proteins may be included, such as albumins, or surfactants, particularly non-ionic surfactants, binding enhancers, e.g. polyalkylene glycols, or the like.

COMPOSITIONS AND METHODS

As previously indicated, the instant invention is directed toward an immunoassay composition which is used in the assay for determining the presence of amphetamines in a sample suspected of containing amphetamine and/or methamphetamine while producing substantially reduced levels of false positives. The immunoassay composition of this invention is able to eliminate the occurrence of a substantial number of false positives by employing an antibody for amphetamine and an antibody for methamphetamine wherein at least one of the antibodies is a monoclonal antibody. The immunoassay can be homogeneous or heterogeneous and can involve a label which is catalytic, chromophoric, fluorescent, radioactive and so forth. The immunoassay composition of this invention is particularly useful in the method described in U.S. Pat. No. 3,817,837. Other methods in which the present immunoassay can be employed include, by way of example and not limitation, those described in "Enzyme-Immunoassay" by Edward T. Maggio, CRC Press Inc., Boca Baton, Fla. 1980, and U.S. Pat. Nos. 3,690,834; 3,791,932; 3,859,578; 3,853,987; 3,867,517; 3,901,654; 3,935,074; 3,984,533; 3,996,345; and 4,098,876.

The compositions of this invention generally comprise two conjugates containing functionally similar labels that are part of a signal producing system wherein one conjugate contains a label bound to a ligand analog of amphetamine and the other conjugate contains a label bound to a ligand analog of methamphetamine. The compositions may include in addition to the conjugates an antibody to amphetamine and an antibody to methamphetamine in an aqueous medium wherein at least one of said antibodies is a monoclonal antibody and optionally other components of the signal producing system. In the absence of amphetamines, the conjugates, when combined in an aqueous solution with the antibodies, bind to the antibodies. When a sample containing amphetamine or methamphetamine is included in the solution, these drugs bind to their respective complementary antibodies and compete with binding of the antibodies to the conjugates thereby generating unbound conjugates in relation to the amount of amphetamines contained in the sample. The unbound conjugate will intrinsically be capable of producing a different signal than the bound conjugate or will be able to produce a different signal as a result of separating the bound and unbound conjugates and therefore as more conjugate becomes unbound a greater change in signal occurs.

In a preferred embodiment, the composition of this invention comprises an antibody to amphetamine, an antibody to methamphetamine, wherein at least one of the antibodies is a monoclonal antibody, and conjugates which are ligand analogs of amphetamine and methamphetamine each covalently or noncovalently bound to a functionally similar label wherein there is moderate cross-reactivity of the monoclonal antibody with that conjugate which binds more strongly with the other antibody. Preferably, both antibodies of this composition are monoclonal antibodies at least one of which is moderately cross-reactive with that conjugate which is more strongly bound by the other monoclonal antibody. Optionally, the composition includes other necessary components of the signal producing system.

The utility of the composition of this invention for the assay of amphetamines where there is moderate cross-reactivity between a monoclonal antibody and its non-complementary conjugate is unexpected because for example, the conjugate of the label with an amphetamine ligand analog which in an assay with one antibody and one conjugate, would be released from binding when amphetamine binds to the antibody, can be bound by the moderately cross- reactive anti-methamphetamine antibody which is present in the assay composition of this invention. Since the amount of unbound conjugate relates to the amount of amphetamines in the sample, the assay response might then be expected to be attenuated. In this regard, reference is made to FIGS. 1a, 1b, 2a, 2b and 3. Concerning FIG. 1a and FIG. 1b, these figures graphically illustrate the change in signal resulting from combining various amounts of amphetamine and methamphetamine with, in the FIG. 1a, a monoclonal antibody for amphetamine, designated 26H8-AMPH, and a conjugate which is a ligand analog of d,l-amphetamine having a label conjugated thereto, and, in FIG. 1b, the same monoclonal antibody for amphetamine and a conjugate which is a ligand analog of d-methamphetamine having a label conjugated thereto. Both conjugates employ an enzyme, specifically glucose-6-phosphate dehydrogenase (G6PDH), as the label. In these assays other members of the signal producing system including the coenzyme NAD and glucose-6-phosphate were added. The y axes correspond to enzyme activity reported as the change in optical density (absorbance) over 30 seconds at a wavelength of 340 nm of a solution wherein the pathlength of light is 2.66 cm; whereas the x axes correspond to the concentrations of amphetamine or methamphetamine in $\mu g/ml$. In the assay when amphetamine is added to the test sample, it competes with the conjugates for binding to the monoclonal antibody and accordingly this increases the amount of unbound conjugates. This results in an increase in enzyme activity because unbound conjugates have a greater enzyme activity than the bound conjugates. As is apparent from FIG. 1A, the increase in enzyme activity correlates to the concentration of amphetamine. For example, a concentration of 0.3 $\mu g/ml$ of amphetamine provides for a change in signal of over 60 units from baseline, i.e., the signal generated by the signal producing system in the absence of any amphetamines, whereas a concentration of 1.0 $\mu g/ml$ of amphetamine provides for a change in signal of over 90 units from baseline.

On the other hand, FIG. 1a further shows that the addition of methamphetamine does not result in an appreciable change in enzyme activity. This is not surprising because the monoclonal antibody used is specific for amphetamine and therefore does not bind to any significant extent to methamphetamine. Since there is no significant binding of the monoclonal antibody with methamphetamine, there should be no increase in the amount of unbound conjugate by the addition of methamphetamine and therefore no change in enzyme activity. Therefore, the absence of appreciable change in enzyme activity is clear evidence that methamphetamine does not bind to any significant extent to the monoclonal antibody for amphetamine.

Figure 1B:
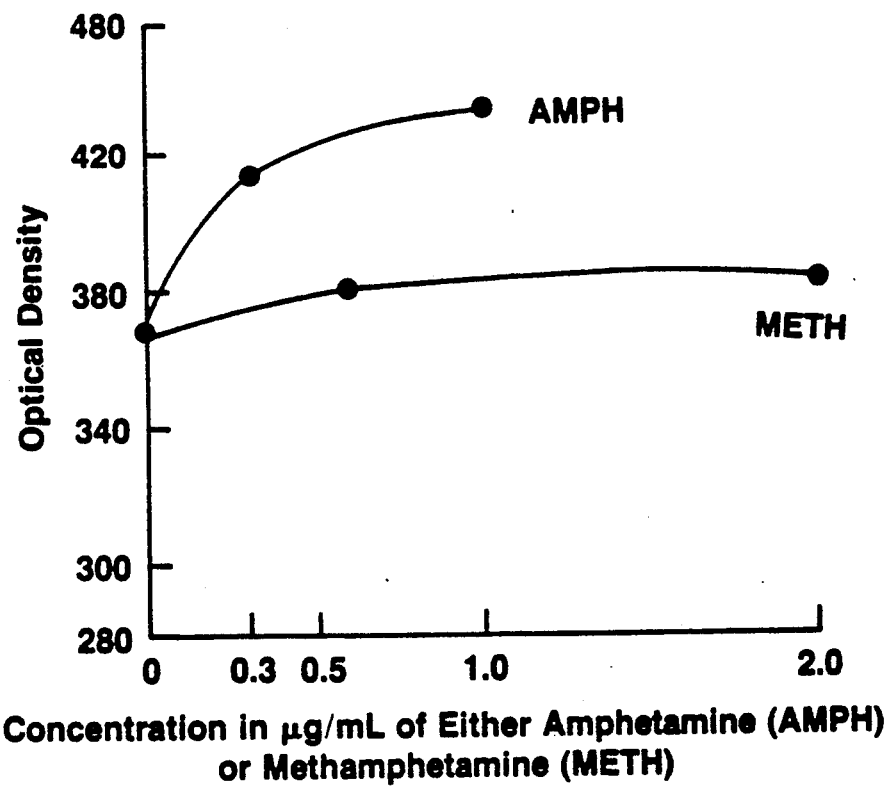

1b employs a monoclonal antibody for amphetamine, designated 26H8-AMPH, and a conjugate of a ligand analog of d-methamphetamine and glucose-6-phosphate dehydrogenase. If the conjugate were not recognized by the monoclonal antibody, neither addition of amphetamine nor methamphetamine would result in an increase in enzyme activity because all of the conjugate would be unbound even in the absence of amphetamines. However, as shown in FIG. 1b, the addition of amphetamine results in an appreciable increase in enzyme activity. This increase is clear evidence that the conjugate containing this ligand analog cross-reacts with the monoclonal antibody for amphetamine and that upon the addition of amphetamine is displaced from the antibody by amphetamine. On the other hand, FIG. 1b further shows that the addition of methamphetamine does not result in any appreciable change in enzyme activity. This shows that while the conjugate containing the ligand analog of methamphetamine cross-reacts with the monoclonal antibody for amphetamine, methamphetamine itself does not.

Figure 2A:
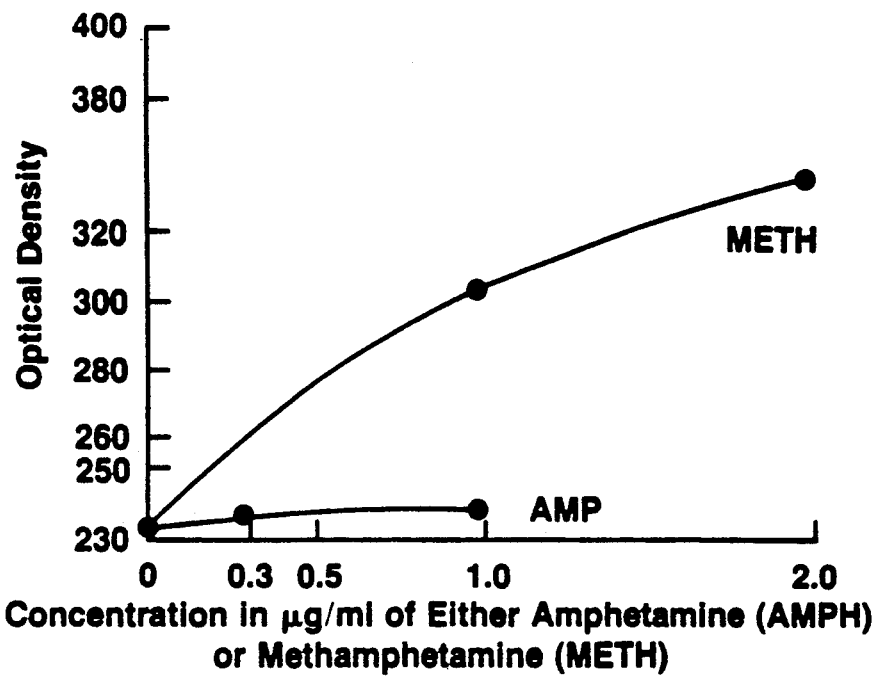
FIG. 2a and FIG. 2b graphically depict the assay responses to amphetamine and methamphetamine in assays utilizing a monoclonal antibody for methamphetamine where the assay of FIG. 2a further utilizes a conjugate of an amphetamine ligand analog with glucose-6-phosphate dehydrogenase and the assay of FIG. 1b further utilizes a conjugate of a methamphetamine ligand analog with glucose-6-phospate dehydrogenase.
Figure 2B:
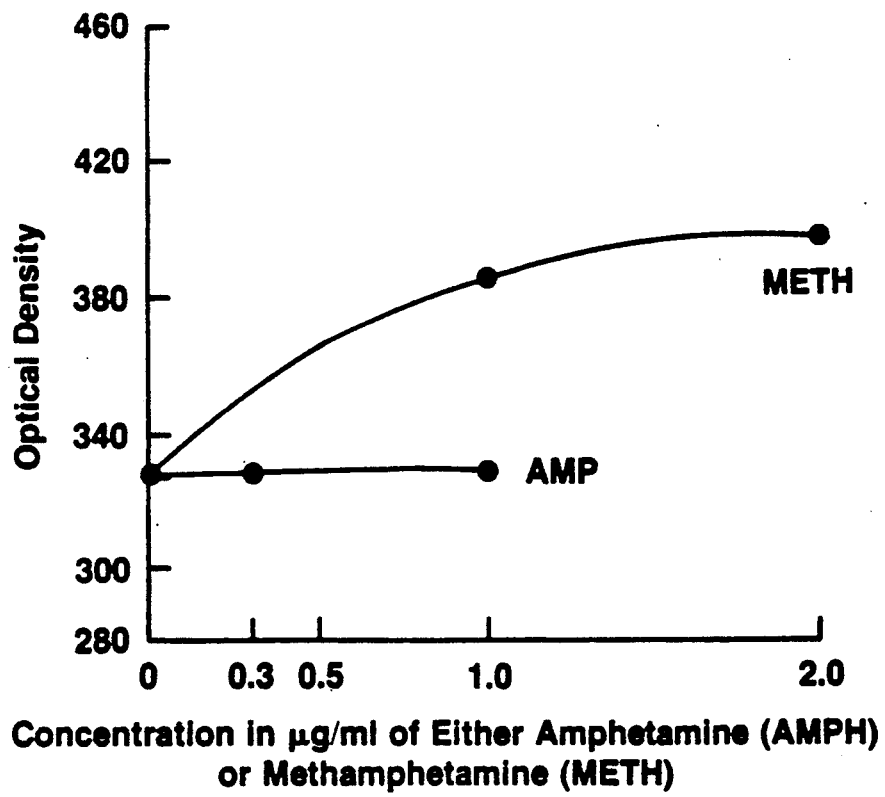
Figure 3:
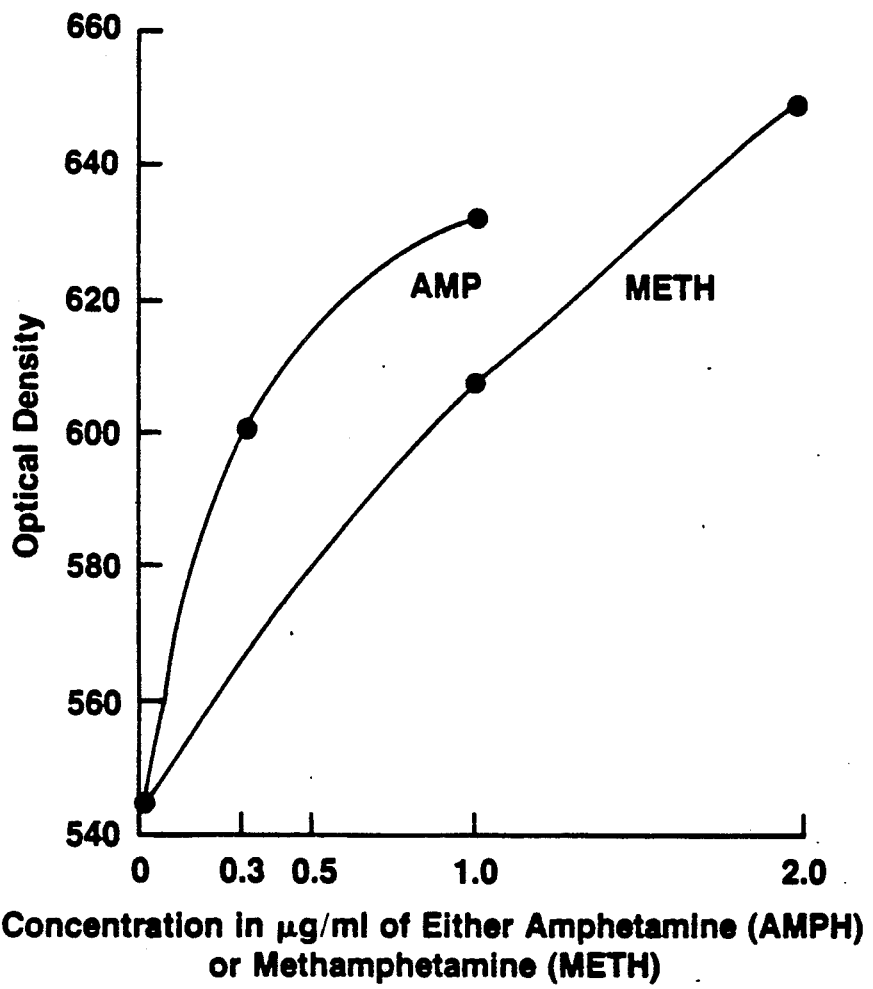
FIG. 3 graphically depicts the signals generated for specified amounts of amphetamine and methamphetamine by the method of this invention.

Concerning FIG. 2a and FIG. 2b, these figures graphically illustrate the change in signal resulting from combining various amounts of amphetamine and methamphetamine with, in FIG. 2a, a monoclonal antibody for methamphetamine, designated 10E12-METH, and a conjugate which is a ligand analog of d-methamphetamine having a label conjugated thereto, and in FIG. 2b, the same monoclonal antibody for methamphetamine and a conjugate which is a ligand analog of d,l-amphetamine having a label conjugated thereto. Both conjugates employ an enzyme, specifically glucose-6-phosphate dehydrogenase (G6PDH), as the label. In these assays, other members of the signal producing system including NAD and glucose-6-phosphate were added. The y axes correspond to enzyme activity reported as the change in optical density (absorbance) over 30 seconds at a wavelength of 340 nm of a solution wherein the pathlength of light is 2.66 cm; whereas the x axis corresponds to the concentration of either amphetamine or methamphetamine in $\mu$g/ml. In the assay when methamphetamine is added to the test sample, it competes with the conjugates for binding to the monoclonal antibody and accordingly this increases the amount of unbound conjugates. This results in an increase in an enzyme activity because unbound conjugates have a greater enzyme activity than the bound conjugates. As is apparent from FIG. 2a the increase in enzyme activity correlates to the concentration of methamphetamine.

On the other hand, FIG. 2a further shows that the addition of amphetamine does not appreciably change the enzyme activity. This is not surprising because the monoclonal antibody used is specific for methamphetamine and therefore will not bind to any significant extent to amphetamine. Since there is no significant binding of the monoclonal antibody with amphetamine, there should be no increase in the amount of unbound conjugate by the addition of amphetamine and therefore no change in enzyme activity. Therefore, the absence of appreciable change in enzyme activity is clear evidence that amphetamine does not bind to any significant extent to the monoclonal antibody for methamphetamine.

FIG. 2b employs a monoclonal antibody for methamphetamine, designated 10E12-METH, and a conjugate of a ligand analog of d,l-amphetamine and glucose-6-phosphate dehydrogenase. If the conjugate were not recognized by the monoclonal antibody, neither addition of amphetamine nor methamphetamine would result in an increase in enzyme activity because all of the conjugate would be unbound even in the absence of amphetamines. However, as shown in FIG. 2b, the addition of methamphetamine results in an appreciable increase in enzyme activity. This increase is clear evidence that the conjugate containing this ligand analog cross-reacts with the monoclonal antibody for methamphetamine and that upon the addition of methamphetamine is displaced from the antibody by the methamphetamine. On the other hand, FIG. 2b further shows that the addition of amphetamine does not result in any appreciable change in enzyme activity. This is taken as further evidence that while the conjugate containing the ligand analog of amphetamine cross-reacts with the monoclonal antibody for methamphetamine, amphetamine itself does not.

In view of the above, it was thought that the cross-reactivity of both conjugates with each antibody would interfere with the signal change produced as a result of the presence of amphetamine or methamphetamine because the antibody that did not recognize the drug in the sample could bind to and inhibit the activity of the conjugate even though the antibody specific for the drug had been effectively prevented from binding to the conjugate.

However, in a preferred aspect of this invention, it has been surprisingly found that cross-reactivity interference appears to be neutralized by combining the conjugate of the label with the ligand analog of amphetamine and the conjugate of the label with the ligand analog of methamphetamine with the monoclonal antibodies specific for amphetamine and methamphetamine. In this regard, reference is made to FIG. 3. This figure graphically illustrates the change in signal resulting from combining either amphetamine or methamphetamine with a monoclonal antibody for amphetamine (designated 26H8-AMPH), a conjugate of a ligand analog of d,l-amphetamine with a label, a monoclonal antibody for methamphetamine (designated 10E12-METH), and a conjugate of a ligand analog of d-methamphetamine with a label and adding other members of the signal producing system. Both conjugates employ an enzyme, specifically glucose-6-phosphate dehydrogenase (G6PDH), as the label and other members of the signal producing system include NAD and glucose-6-phosphate. As shown in FIGS. 1a, 1b, 2c and 2d, both the monoclonal antibody for amphetamine and the monoclonal antibody for methamphetamine cross-react with the two conjugates containing the amphetamine ligand analog and the methamphetamine ligand analog. In the graph of this figure, the x and y axes correspond to the same parameters as in the preceding graphs.

As in the preceding assays, an increase in the amount of unbound conjugate produces an increase in enzyme activity. This first curve on this graph illustrates the relation between the concentration of amphetamine and the enzyme rate whereas the second curve illustrates the relation between the concentration of methamphetamine and the enzyme rate. In both cases, the curves illustrate that there is a strong signal generated that is related to the concentration of both amphetamine and methamphetamine. Accordingly, FIG. 3 demonstrates that the composition of this invention can be used to assay for amphetamines by using a monoclonal antibody for amphetamine, a monoclonal antibody for methamphetamine, and two conjugates each containing a functionally similar label wherein one label is bound to a ligand analog of amphetamine and the other label is bound to a ligand analog of methamphetamine wherein there is moderate cross-reactivity between both monoclonal antibodies and the conjugates employing noncomplementary ligand analogs.

Moreover, the composition of this invention can also be used to assay a sample containing both amphetamine and methamphetamine. While it would not be possible to determine whether the signal increase was due to amphetamine, methamphetamine or a combination thereof, the increase in signal would nevertheless be a positive indication of the presence of amphetamines in the sample.

This is an appropriate point to discuss the maximum extent of cross-reactivity permitted by the composition of this invention which employs conjugates which are ligand analogs of amphetamine and methamphetamine bound to functionally equivalent labels. In particular, it is noted that the definition of moderate cross-reactivity employs a range of 20–80%. The upper limit of 80% is necessary because at this point so much of the antibody can bind to the moderately cross-reactive conjugate that upon addition of the drug that binds to the antibody that is complementary to the moderately cross-reactive conjugate, much of the conjugate that would otherwise no longer be bound becomes bound by the cross-reactive antibody. Thus there is very little change in the signal even in the presence of drug. In view of the above, in a composition employing two antibodies and two conjugates it is necessary that moderate cross-reactivity not exceed 80% and preferably should not exceed about 60% and even more preferably should not exceed about 50%.

In another preferred aspect of this invention, the concentrations of the antibodies and conjugates are adjusted so as to provide the same signal change for a predetermined minimum amount of amphetamine and for a predetermined minimum amount of methamphetamine. In such a case, the person conducting the assay can determine whether the sample is positive for the presence of at least the predetermined minimum amount of amphetamine or methamphetamine without regard to which drug is in fact present.

In a preferred embodiment of this invention, conjugates containing an enzyme label ("enzyme conjugates") are used that have greatly reduced enzyme activity when bound by anti-ligand antibody. Preferably, the fraction inhibition by antibody of the enzyme conjugates is at least 0.50 and more preferably at least 0.65–0.80. As used herein the term "fraction inhibition of an enzyme conjugate" means 1 minus the ratio of the minimum enzyme rate observed as increasing amounts of antibody are added to the conjugate divided by the rate in the absence of antibody.

The manner of conducting an assay for amphetamines in a sample suspected of containing amphetamine and/or methamphetamine comprises combining in an aqueous medium (a) the sample; (b) an antibody to amphetamine and an antibody to methamphetamine wherein at least one of the antibodies is a monoclonal antibody; (c) two conjugates, each containing a functionally similar label one bound to a ligand analog of amphetamine and the other bound to a ligand analog of methamphetamine; and (d) any other necessary components of the signal producing system under conditions allowing the antibodies to bind to the conjugates as a function of the amount of amphetamine and methamphetamine in the sample, wherein a signal is produced that is related to the amount of amphetamines in the sample, and determining the signal.

The solvent for this assay is an aqueous medium, which may contain up to about 40 weight percent of other polar solvents, particularly oxygenated solvents of from 1 to 6, more usually of from 1 to 4 carbon atoms, including alcohols, ethers and the like. Usually, the cosolvents will be present in less than about 20 weight percent. Under some circumstances depending on the nature of the sample, some or all of the aqueous medium could be provided by the sample itself.

The pH for the medium will usually be in the range of 4–11, more usually 5–10, and preferably in the range of about 6–9. The pH is chosen to provide optimum binding of the binding members and optimal generation of signal by the signal producing system. Various buffers may be used to achieve the desired pH and maintain the pH during the assay. Illustrative buffers include borate, phosphate, carbonate, tris, barbital and the like. The particular buffer employed is not critical, but in individual assays, one buffer may be preferred over another.

For certain assay protocols, desirably, from about 0.05 to 0.5 weight percent of a non-ionic detergent is included with the sample. Various polyoxyalkylene compounds may be employed of from about 200 to 20,000 daltons.

Moderate temperatures are normally employed for carrying out the assay. The temperatures for the assay and production of a detectable signal will generally be in the range of about 4°–50° C., more usually in the range of about 10°–40° C., and frequently will be ambient temperatures, that is, about 15°–25° C.

The concentration is the aqueous test solution of amphetamines that may be assayed will generally vary from about $10^{-4}$ to about $10^{-10}$M, more usually from about $10^{-5}$ to $10^{-9}$M. Considerations, such as the protocol employed will normally determine the concentration of the other reagents.

While the concentrations of many of the various reagents in the sample and reagent solutions will generally be determined by the concentration range of interest of the analyte, the final concentration of each of the reagents will normally be determined empirically to optimize the sensitivity of the assay over the range of interest. With certain protocols, individual reagents may be used in substantial excess without detrimentally affecting the sensitivity of the assay.

In carrying out the assay, the order of addition is not critical although the protocol will normally involve first combining in an aqueous medium the sample suspected of containing amphetamines with the antibodies for amphetamine and methamphetamine followed by addition of the two conjugates. Alternatively, the conjugates and antibodies can be added simultaneously to the sample or the sample and conjugates can be combined followed by addition of the antibodies. The mixture is then maintained under conditions allowing the antibodies to bind to the conjugate as a function of the amount of amphetamine and methamphetamine in the sample. As discussed above, this is accomplished by maintaining the sample at an appropriate temperature, pH, etc., for a period of time generally less than 1 hour and preferably from about 2 seconds to 10 minutes. If the assay procedure is homogenous, then at this time there is added to the sample any necessary components of the signal producing system that are not already present and the signal is then determined. On the other hand if the assay procedure is heterogenous, then at this time the conjugates which are bound to antibody are separated from unbound conjugates. Any necessary components of the signal producing system are then added to one of the separated fractions and the signal is then determined. In both cases, the resulting signal is related to the signal generated by a sample or calibrator with a predetermined amount of amphetamine and/or methamphetamine present or by a negative sample or calibrator. Determination of the signal is accomplished by exposing the sample to the signal producing means.

Also as discussed above, the amounts of each of the components employed in the assay can be selected based on the predetermined minimum amounts of amphetamine and methamphetamine that the assay is testing for as well as the level of signal desired. The result of the assay will indicate whether any amphetamines are present but not which one.

As a matter of convenience, the assay composition of the present invention can be provided in a kit in packaged combination with predetermined amounts of the reagents employed in assaying for amphetamines. As noted above, these components include an antibody for amphetamine, an antibody for methamphetamine, conjugates employing ligand analogs complementary to these antibodies and any necessary components of the signal producing system wherein at least one of the antibodies is a monoclonal antibody. In addition, other additives such as ancillary reagents may be included, for example, stabilizers, buffers, and the like. The relative amounts of the various reagents may be varied widely, to provide for concentrations in solution of the reagents which substantially optimize the sensitivity of the assay. The reagents can be provided in solution or as dry powders, usually lyophilized, including excipients, which on dissolution will provide for a reagent solution having the appropriate concentrations for performing the assay.

COMPOUNDS

The compositions of this invention are directed to conjugates and antibodies for use in an amphetamine/methamphetamine assay. Accordingly, in this regard, one embodiment of the instant invention is directed to certain compounds which can be used in the assay or are precursors to compounds so used. Therefore, in its compound aspect, the instant invention is directed toward a compound of the formula I:

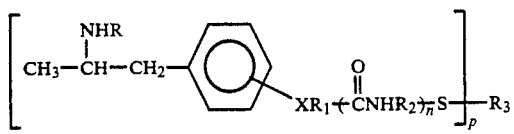

wherein:

R is hydrogen or methyl;
X is oxygen, sulfur or a bond;
$R_1$ is alkylene of 1 to 6 carbon atoms;
$R_2$ is alkylene of 2 to 6 carbon atoms;
n is 0 or 1;
$R_3$ is hydrogen, $-SR_4$ wherein $R_4$ is alkyl of from 1 to 6 carbon atoms, or is $(A)_pZ$ wherein A is derived from a functionality capable of reacting with a thiol group to form a bond between the sulfur atom of the thiol group and A, and Z is a poly(amino acid); and
p is 1 when $R_3$ is hydrogen or $-SR_4$ and is a number from 1 to the molecular weight of the poly(amino acid) divided by 500 when $R_3$ is $(A)_pZ$;

and with the proviso that when n is zero $R_1$ is alkylene of 2 to 6 carbon atoms and with the further proviso that the benzene ring is bonded to X at the meta or para position to the

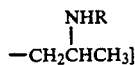

group and when X is a bond, the benzene ring is bonded to X at the para position.

When n is zero and $R_3$ is $-SR_4$, the compounds of this invention have the following formula II:

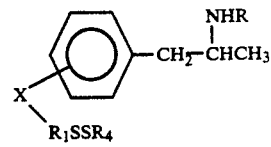

wherein R, $R_1$, $R_4$ and X are as defined above. When X is oxygen or sulfur, compounds of formula II can be prepared from 3-hydroxyphenyl acetone, 3-mercaptophenyl acetone, 4-hydroxyphenyl acetone and 4-mercaptophenyl acetone which in turn can be prepared by acetylating 3- or 4-hydroxyphenyl acetic acid or 3- or 4-mercaptophenyl acetic acid followed by decarboxylation and hydrolysis. 3- or 4-hydroxyphenyl acetone or 3- or 4-mercaptophenyl acetone is then treated with sodium or potassium carbonate followed by reaction with $YR_1SSR_4$ wherein Y is halo, preferably chloro or bromo, and $R_1$ and $R_4$ are as defined above. The resulting product is then reacted with ammonium acetate or methylamine followed by reaction with a reducing agent such as sodium cyanoborohydride to form the amphetamine analog or the methamphetamine analog of formula II above. The compound $YR_1SSR_4$ can be prepared by reacting $YR_1SH$ and $R_4SS(O)_2CH_3$ under conditions to form the desired disulfide product.

Alternatively, compounds of formula II above wherein X is S can be prepared from 3- or 4-nitrophenyl acetone which in turn can be prepared by acetylating 3- or 4-nitrophenyl acetic acid followed by decarboxylation and hydrolysis. The 3- or 4-nitrophenyl acetone is reacted with ammonium acetate or methylamine followed by reaction with a reducing agent such as sodium cyanoborohydride to form the nitro amphetamine or nitro methamphetamine analog. Next, the nitro group is reduced by reaction with sodium dithionite to the amine which is then converted to the diazonium salt by reaction with nitric acid in dilute sulfuric acid. Reaction of the diazonium salt with $HSR_1SH$ followed by formation of a disulfide by reaction with $R_4SS(O)_2CH_3$ yields the disulfide derivative of formula II. In formula I when $R_3$ is Z, i.e., a poly(amino acid), the reaction of the diazonium salt with $HSR_1SH$ can be followed by reaction with a poly(amino acid) which has been functionalized to form $(A)_pZ$ so as to be reactive with thiol groups. A can for example be bromo or iodoacetyl, (N-maleimidyl)-cyclohexylcarbonyl, or (N-maleimidylmethyl)benzoyl bonded to an amino group of the polyamino acid to form a stable amide.

When X is a bond, compounds of formula II can be prepared by derivatizing the carboxylic acid group at the meta or para position of m- or p-carboxylphenyl acetic acid by using techniques known in the art. Alternatively, these compounds can be prepared by starting with m- or p-halophenyl acetic acid by reacting these compounds with an alkyl metal or metal hydride, such as alkyl lithium or potassium hydride, which forms a metal salt which is then converted to the appropriate side chain by reaction with $YR_1SSR_4$ where Y, $R_1$ and $R_4$ are as defined above. In either case, the acetic acid moity is then converted to an amphetamine or methamphetamine side chain by the procedures set forth above.

When n is one, X is a bond and $R_3$ is $-SR_4$, the compounds of this invention have the following formula III:

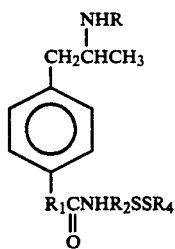

III wherein R, $R_1$, $R_2$, and $R_4$ are as defined above. Compounds of formula III can be prepared from amphetamine and methamphetamine by first protecting the amino or methylamino group with a suitable blocking group followed by reaction with aluminum trichloride and $YC(O)R_1C(O)_2R_5$ wherein $R_1$ and Y are as defined above and $R_5$ is alkyl of from 1 to 6 carbon atoms to form the $-C(O)R_1C(O)_2R_5$ ester at the p-position of the phenyl group, which is then hydrolyzed to form the acid, i.e., $-C(O)R_1C(O)_2H$, Next the carbonyl is reduced and then the acid functionality is activated for example by forming an activated ester which is then reacted with $NH_2R_2SSR_4$ to form the amide. The protecting group is then removed which additionally can convert the disulfide group, i.e., $R_3=SR_4$, to the thiol group, i.e., $R_3=H$. When $R_3$ is destined to be a poly(amino acid), the thiol compound can be immediately reacted with a poly(amino acid) which has been functionalized so as to be reactive with thiol groups or if storage of this product for future use is desired, then it can be converted to a dithio product of Formula III above by reaction with $R_4SS(O)_2CH_3$.

Compounds of the formula $NH_2R_2SSR_4$ are prepared by reacting $NH_2R_2SH$ with $R_4SS(O)_2CH_3$ under conditions to form the desired disulfide product.

When $R_1$ is alkylene of 1 to 6 carbon atoms, n is 1, $R_3$ is $-SR_4$ and X is not a bond, the compounds of this invention have the following formula IV:

IV wherein R, $R_1$, $R_2$ and $R_4$ are as defined above and X' is oxygen or sulfur. Compounds of formula IV can be prepared from 3-hydroxyphenyl acetone, 3-mercaptophenyl acetone, 4-hydroxyphenyl acetone and 4-mercaptophenyl acetone by first reacting 3- or 4-hydroxyphenyl acetone or 3- or 4-mercaptophenyl acetone with $YR_1CO_2R_5$ wherein Y is halo, preferably bromo or chloro, and $R_5$ is hydrogen or alkyl of 1 to 6 carbon atoms, preferably t-butyl. In some cases, it may be necessary to first add sodium or potassium carbonate prior to reaction with $YR_1CO_2R_5$. In any event, the resulting product is hydrolyzed to form the acid which is then activated for example by forming an activated ester and reacting it with $NH_2R_2SSR_4$ to form the corresponding amide. The product is then reacted with ammonium acetate or methylamine followed by reaction with a reducing agent such as sodium cyanoborohydride to form the amphetamine analog or the methamphetamine analog of formula IV above.

Certain compounds of this invention can be prepared which are optical isomers of amphetamine and methamphetamine. Such optical isomers can be prepared from optical isomers of amphetamine, methamphetamine or optically active precursors thereof, i.e., d-m-hydroxyephedrine, d-metaraminol, etc., which are converted to optical isomers of amphetamine or methamphetamine by art recognized techniques. In such cases, the amine (or methylamine) attached to the optically active carbon atom is first protected by a conventional protecting group such as t-butoxycarbonyl (t-boc) and the compound is then derivatized by the procedures outlined above to provide a suitable substituent group at the meta or para position of the phenyl group and then the protecting group is removed to yield the corresponding optically active isomers.

When $R_3$ is $(A)_pZ$, the amphetamine and methamphetamine analogs are linked to a poly(amino acid), Z, by the linking group, A, wherein A is derived from a functionality capable of reacting with a thiol group.

The molecular weight of the poly(amino acids) will generally be at least about 5,000 and have no upper limit, normally being less than 10,000,000, and usually being not more than about 600,000. There will usually be different ranges depending on whether an antigen or an enzyme is involved. With antigens, the range will be from about 5,000 to 10,000,000, usually from about 20,000 to 600,000, and more usually from about 25,000 to 250,000 molecular weight. With enzymes, the range will be from about 10,000 to 600,000, and more usually from about 10,000 to 300,000 molecular weight. For both antigens and enzymes, there will usually be at least about 1 amphetamine or methamphetamine analog group per 200,000 molecular weight, more usually at least one per 50,000 molecular weight. In the case of intermediate weight antigens (35,000 to 600,000), the number of amphetamine or methamphetamine analog groups will generally be from about 2 to 250, more usually from 10 to 100. With lower molecular weight antigens, (below 35,000), the number of amphetamine or methamphetamine analog groups will generally be in the range from about 2 to 10, usually in the range from 2 to 5.

Various protein types may be employed as the poly(amino acid) antigenic material. These types include albumins, serum proteins, e.g., globulins, ocular lens proteins, lipoproteins, and the like. Illustrative proteins include bovine serum albumin, keyhole limpet hemocyanin, egg ovalbumin, bovine gamma-globulin, and the like. Alternatively, synthetic poly(amino acids) may be prepared having sufficient available amino groups, e.g., lysines.

The enzymes can vary widely, depending on the ease of conjugation, turnover rate, and the physiological fluid in which the amphetamines are to be measured. Suitable enzymes are set forth above. Particularly preferred are those enzymes which employ nicotinanide adenine dinucleotide (NAD), or its phosphate (NADP) as a cofactor, particularly the former, or the reduced forms thereof. Illustrative of these enzymes is glucose-6-phosphate dehydrogenase.

The antigen and enzyme conjugates can be conveniently prepared by first reacting these poly(amino acids) with a linking group which is also capable of reacting with a thiol group, i.e., bromoacetic acid, chloroacetic acid, activated esters thereof, etc. The resulting product has an active halogen which is capable of reacting with the thiol group of formula I, i.e., $R_3=H$. The thiol group of formula I is readily prepared by reacting the disulfide, i.e., $R_3=SR_4$, under reduction conditions suitable to form the thiol. The thiol product is generally formed just prior to reaction with the functionalized poly(amino acid) in order to avoid undesired formation of disulfide.

By employing the procedures to be exemplified, the amine and methylamine moieties present on amphetamine and methamphetamine respectively are retained during the conjugation procedure. These moieties, which provide for a distinction between closely similar compounds, are exposed and result in formation of antibodies having low or minimal recognition for with structurally similar compounds.

Polyclonal antibodies can be prepared by injecting the antigen conjugate into a wide variety of vertabrates in accordance with conventional methods for the production of antibodies. Usually, the animals are bled periodically, with successive bleeds having improved titer and specificity, until reaching a plateau and then diminishing in their specificity and titer. The antigen conjugate may be injected intramuscularly, intraperitoneally, subcutaneously, or the like. Usually a vehicle is employed, such as complete or incomplete Fruend's adjuvant.

Likewise, monoclonal antibodies useful in this invention may be produced according to the standard techniques of Kohler and Milstein, *Nature* 265: 495–497, 1975. For example, the antigen conjugate is injected into a mouse and, after a sufficient time, the mouse is sacrificed and spleen cells obtained. The spleen cell chromosomes encoding the base sequences for the desired immunoglobulins are immortalized by fusing the spleen cells, generally in the presence of a non-ionic detergent, for example, polyethylene glycol. The resulting cells, which include the fused hybridomas, are allowed to grow in a selective medium, such as HAT-medium, and the surviving cells are grown in such medium using limiting dilution conditions. The cells are grown in a suitable container, e.g., microtiter wells, and the supernatant is screened for monoclonal antibodies having the desired specificity.

Various techniques exist for enhancing yields of monoclonal antibodies, such as injection of the hybridoma cells into the peritoneal cavity fo a mammalian host, which accepts the cell, and harvesting the ascites fluid. Where an insufficient amount of the monoclonal antibody collects in the ascites fluid, the antibody is harvested from the blood of the host. Various conventional ways exist for isolation and purification of the monoclonal antibodies from other proteins and other contaminants (see Kohler and Milstein, supra).

The following examples are offered by way of illustration and not by way of limitation.

In these examples, reference to parts per million (ppm) in the Nuclear Magnetic Resonance (NMR) spectra refers to ppm downfield from tetramethyl silane (TMS).

All temperatures not otherwise indicated are centigrade.

The following abbreviations are used:
G6PDH-glucose-6-phosphate dehydrogenase;
BSA-bovine serum albumin;
KLH-keyhole limpet hemocyanin;
tlc-thin layer chromatography;
G6P-glucose-6-phosphate;
NAD-nicotinamide adenine dinucleotide;
NADH-reduced nicotinamide adenine dinucleotide;
RSA-rabbit serum albumin;
CDCl$_3$-deuterated chloroform;
CD$_3$OD-deuterated methanol;
DMSO-dimethylsulfoxide;
D$_2$O-deuterated water.
CFA-Complete Freund's Adjuvant;
DMEM-Dulbecco's Modified Eagle's Medium;
ELISA-Enzyme-linked Immunosorbent Assay;
HBSS-Hanks Balanced Salt Solution;
HT media-Super DMEM with 0.1 mM hypoxanthine, 16 $\mu$M thymidine (50× stock from Sigma)
HAT media-HT media with 0.8 $\mu$M aminopterin (50× HAT stock from Sigma)
ip-intraperitoneal injection;
iv-intravenous injection;
sc-subcutaneous injection;
IFA-incomplete Freund's Adjuvant;
NSS-normal sheep serum;
PBS-phosphate buffered saline, pH 7.2;
Super DMEM-DMEM with 10% fetal calf serum, 10% NCTC 109, 50 mg/ml gentamicin, 4.0 mM L-glutamine, 1.0 mM oxaloacetic acid, 0.45 mM pyruvate, 2.5 IU/liter bovine insulin wash buffer and 0.05% Tween 20 in PBS.

EXPERIMENTAL

COMPOUNDS

1. Preparation of d,1-m-(mercaptoethylamidomethoxy)amphetamine

A. Preparation of m-hydroxyphenyl acetone

A solution of m-hydroxyacetic acid (60 g, 0.395 mole) in acetic anhydride (146 ml) and pyridine (146 ml) was refluxed overnight using a round bottom flask to which was attached a reflux condenser and a calcium sulfate drying tube. Complete reaction was observed by the disappearance of starting material using tlc (silica gel eluted with 1:9 parts by volume methanol:methylene chloride). The product was then evaporated to dryness under vacuum at 40°. The residue was hydrolyzed by adding ethanol (anhydrous, 225 ml) and concentrated hydrochloric acid (22.5 ml), and the brown solution was then refluxed for 2 hours and then cooled and kept in the freezer overnight for convenience.

The resulting solution was diluted with water, and the aqueous solution was extracted with methylene chloride (a total of 600 ml). The organic extracts were combined, washed with saturated sodium chloride solution (1×20 ml), 5% sodium bicarbonate solution (1×20 ml), and saturated sodium chloride solution (1×30 ml). The methylene chloride solution was dried over sodium sulfate and the solvent was evaporated off to yield the title compound as an oily product.

A small amount of this product was purified by chromatography on preparative thick layer chromatography plates which were eluted with a 1:1 parts by volume ethyl acetate:hexane. The desired band was recovered, washed with ethyl acetate and the solution evaporated under vacuum to yield pure title compound. NMR in CDCl$_3$ shows a 3 proton singlet at 2.35 ppm; 2 proton singlet at 3.65 ppm; 2 proton multiplet at 6.65–6.85 ppm; 1 proton doublet of doublets at 7.3 ppm; 1 proton singlet at 8 ppm. The UV of the product shows a bathochronic shift in pH8 and in alkaline solution ($\lambda_{max}$273 nm-pH8; $\lambda_{max}$293 nm-1N NaOH).

B. Preparation of m-(t-butylcarboxymethoxy)phenyl acetone

To a solution of m-hydroxyphenyl acetone (10.0 g, unpurified product from A above) in 100 ml of tetrahydrofuran was added potassium carbonate (7 g) and t-butylbromoacetate (12 ml). The resulting suspension was allowed to stir at room temperature overnight. An aliquot of the reaction mixture was withdrawn and spotted on tlc (silica gel eluted with 1:4 parts by volume ethyl acetate:hexane). It showed the formation of only a small amount of new product. Therefore, additional amounts of potassium carbonate (3 g) and t-butylbromoacetate (8 ml) were added. The resulting system was allowed to stir at room temperature until the complete reaction was observed (or up to a maximum of 4 days). The precipitates were filtered off, and to the solution was added silica gel (about 30 g, EM flash column silica gel). The resulting suspension was placed on a column of silica gel (2"×8") and eluted with hexane until the complete elution of the t-butylbromoacetate starting material. Then the column was eluted using 1:19 parts by volume ethyl acetate:hexane until a majority of desired product, m-(t-butylcarboxymethoxy)phenyl acetone, had been eluted out. Ethyl acetate was then used to elute the small amount of product remaining on the column. The product was combined into two fractions and the solvent evaporated; one fraction of pure title compound (6.7 g) and another fraction of title compound (4.8 g) which contained a small amount of impurity. If necessary, this second fraction could be further purified. NMR of the pure compound in CDCl$_3$ shows a 9 proton singlet at 1.49 ppm; a 3 proton singlet at 2.14 ppm; a 2 proton singlet at 3.65 ppm; a 2 proton singlet at 4.51 ppm; a 3 proton multiplet at 6.69 ppm and a 1 proton multiplet at 7.26 ppm. The UV of the title product showed no bathochronic shift in pH8 and in 0.1N NaOH ($\lambda_{max}$271 in both cases).

C. Preparation of m-(carboxymethoxy)phenyl acetone

To m-(t-butylcarboxymethoxy)phenyl acetone, 6.7 g, was added trifluoroacetic acid (40 ml) at room temperature under nitrogen. After five minutes, reaction was found to be completed by tlc (silica gel eluted with 1:9 parts by volume methanol:methylene chloride) and the solvent was then evaporated to dryness. The resulting brown oil showed the desired product and trace of starting material on tlc. IR showed characteristic carboxylic acid peak at 3600–2450 cm$^{-1}$.

D. Preparation of methyldithioethylamine hydrochloride

A solution of methyl methanethiol sulfonate (6 g, 0.0396 mole) in 10 ml of methanol (degassed by bubbling nitrogen for at least 10 minutes) was added dropwise to a solution of 2-aminoethanethiol hydrochloride (4.3 g, 0.0380 mole) in 10 ml of methanol (also degassed). The addition took about half an hour. Afterwards, the resulting solution was allowed to stir at room temperature for two hours and tlc (silica gel eluted with 1:9 parts by volume methanol:methylene chloride) of an aliquot of the solution showed complete reaction. The resulting solution was then evaporated to dryness and the white solid thus obtained was then triturated using ether (100 ml), and the crude product was collected using suction filtration and dried overnight under vacuum. The crude product (6.2 g) was dissolved in methanol and mixed with 20 g silanized silica gel RP-2 (EM reagent 70–230 mesh). The resulting suspension was then evaporated to dryness and was then placed on a column containing silanized silica gel (RP-2, 2 in.×8 in., EM reagent, particle size 70–230 mesh). The column was eluted, using 1 liter methylene chloride and then with 1:19 parts by volume methanol: methylene chloride until the title compound was obtained. Evaporation of the solvent gave 4.8 g of the title compound as a white solid. NMR of this product in CD$_3$OD shows a 3 proton singlet at 2.45 ppm; a 2 proton triplet at 3.06 ppm; and a 2 proton multiplet at 3.3 ppm.

E. Preparation of m-(methyldithioethylamidomethoxy)phenyl acetone

To a solution of m-(carboxymethoxy)phenyl acetone (6.1 g, 0.029 mmole) in N,N-dimethylformamide (56 ml, dried over molecular sieves, 3A) were added under nitrogen at 5° powdered 1-ethyl-3-(3-dimethylaminopropyl)carbodiimide hydrochloride (EDCI, 6.1 g, 0.032 mole) and N-hydroxysuccinimide (3.7 g, 0.032 mole). The resulting reaction mixture was then allowed to stir at 5° overnight. The complete formation of N-hydroxysuccinimic ester was observed. To the methyldithioethylamide hydrochloride (4.7 g, 0.029 mole, prepared in D above) in water (20–50 ml) was added triethylamine to adjust the pH to 8.5. Then the N-hydroxysuccinimic ester of m-(carboxymethoxy)phenyl acetone was added dropwise to the methyldithioethylamine solution with the adjustment of pH to 8.5, and the resulting solution was allowed to stir at 5° for 1 hour. Additional reagents, methyldithioethylamine hydrochloride (2 g, 0.0125 mole) and EDCI (3.0 g, 0.0156 mole), were added and the pH of the resulting solution was adjusted to 6.5 and the reaction mixture was allowed to stir at 5° overnight.

The product was diluted with water, and the resulting solution was extracted using methylene chloride, dried over sodium sulfate and the solvents evaporated under vacuum to give a dark oil which was then dissolved in a minimum amount of methylene chloride. The resulting solution was then added to silica gel (20 g, EM flash column silica gel). The suspension thus obtained was evaporated to dryness, and the dried silica gel was placed on a column containing silica gel (2 in.×8 in., EM flash column silica gel) and then sand was added (~0.5–1.0 inch) on the top of the silica gel. The column was then eluted using 1:1 parts by volume ethyl acetate: hexane. The title product (4.6 g) was obtained which was further purified on preparative thick layer silica gel plates (silica gel GF, eluted with 1:1 parts by volume ethyl acetate: hexane). The desired band was recovered, washed with 1:4 parts by volume methanol: methylene chloride and the solution evaporated to give 4.3 g of the title product. NMR in CDCl$_3$ shows a 3 proton singlet at 2.18 ppm; a 3 proton singlet at 2.41 ppm; a 2 proton triplet at 2.85 ppm; a 4 proton multiplet at 3.69 ppm; a 2 proton singlet at 4.50 ppm; a 3 proton multiplet at 6.69–6.91 ppm; and a 1 proton multiplet at 7.40 ppm.

F. Preparation of d, 1-m-methyldithioethylamidomethoxy)amphetamine

To a solution of m-(methyldithioethylamidomethoxy)phenyl acetone (680 mg, 2.17 mmoles) in methanol (21 ml, degassed by bubbling with nitrogen for 15 minutes) was added ammonium acetate (834 mg, 10.8 mmoles) at room temperature under nitrogen. After half an hour, sodium cyanoborohydride (152 mg, 2.42 mmoles) was added into the resulting solution under nitrogen. After two and a half hours, disappearance of the starting material was observed on tlc (silica gel or alumina, 1:9 parts by volume, methanol:methylene chloride). To the reaction product was then added slowly glacial acetic acid (12 ml) to adjust the pH of the system to 4.6. The resulting product was concentrated using a rotary evaporator to remove methanol, and to the solution thus obtained was added sodium chloride (about 1 g) and water (about 5 ml). The resulting solution was then extracted using methylene chloride and the resulting methylene chloride solution dried over sodium sulfate. The solution was then evaporated to give a light yellow oil which was purified by chromatography on preparative thick layer chromatography plates (EM aluminum oxide, eluted with 1:9 parts by volume methanol:methylene chloride). The desired band was recovered, washed with 1:4 parts by volume methanol:methylene chloride and the solution evaporated and dried under vacuum at room temperature to give the title product (234 mg). NMR of this product in CDCl$_3$ shows a three proton doublet at 1.26 ppm; a 3 proton singlet at 2.41 ppm; a 4 proton multiplet at 2.86 ppm; a 1 proton multiplet at 3.52 ppm; a 2 proton triplet at 3.61 ppm; a 2 proton singlet at 4.53 ppm; a 3 proton multiplet at 6.90 ppm; and a 1 proton triplet at 7.3 ppm.

This compound was then stored under argon at 0°.

G. Preparation of d,1-m-(mercaptoethylamidomethoxy)amphetamine

To d,1-m-(methyldithioethylamidomethoxy)amphetamine (30 mg, 0.096 mmole-from F above) in 0.64 ml of methanol (degassed with argon) was added dithioerythritol (DTE, 14 mg, 0.090 mmole) in 1 ml of methanol (degassed with argon) and then triethylamine (12 µl) under argon at room temperature. After two hours, an aliquot was withdrawn spotted on tlc (silica gel, eluted with 1:4 parts by volume methanol methylene chloride); it showed the formation of the title compound when the tlc was sprayed using Ellman's reagent (yellow spot).

The solvent was then evaporated to dryness, then an additional amount of methanol (1 ml—degassed with argon) was added, and the solvent was again evaporated. The resulting product was then dried under reduced pressure using a vacuum pump at room temperature to yield the title compound.

2. Preparation of d,1-m-(mercaptoethylamidomethoxy)methamphetamine

A. preparation of d,1-m-(methyldithioethylamidomethoxy)methamphetamine

To a solution of m-(methyldithioethylamidomethoxy)phenyl acetone (680 mg, 2.17 mmoles—prepared in a manner similar to Steps A-E of Example 1) in methanol (21 ml, degassed by bubbling nitrogen for 15 minutes) was added methylamine hydrochloride (818 mg, 12.1 mmoles) at room temperature under nitrogen. After one hour, sodium cyanoborohydride (136 mg, 2.17 mmoles) was added, and the resulting clear solution was allowed to stand at room temperature under nitrogen. After three hours, disappearance of starting material was observed on tlc (silica gel eluted with 1:9 parts by volume methanol:methylene chloride; alumina oxide, type E 60F-254, eluted with 1:24 parts by volume methanol:methylene chloride). To the reaction product was then added slowly glacial acetic acid to give the solution a pH of 4–4.2. The resulting product was concentrated using a rotary evaporator to remove methanol and then a small amount of water was added (about 5 ml). The resulting solution was then extracted using methylene chloride. Evaporation of the solvents gave the title compound as a crude oily product.

The product was purified by first dissolving in a small amount of methylene chloride and chromatographing this solution on preparative thick layer chromatography plates (EM aluminum oxide, type E, eluted with 1:24 parts by volume methanol:methylene chloride). One-half of the plates showed a product of high purity, and the desired band was recovered, washed with 1:4 parts by volume methanol:methylene chloride and the solution evaporated to yield 167 mg of the title product. Title product was also recovered from the other remaining plates and rechromatographed using the same conditions described above to yield 232 mg of additional compound. Total yield=399 mg. NMR in CD$_3$OD shows a 3 proton doublet at 1.20 ppm; a 3 proton singlet at 2.40 ppm; a 3 proton singlet at 2.71 ppm; a 2 proton triplet at 2.84 ppm; a 3 proton triplet at 3.60 ppm; a 2 proton singlet at 4.54 ppm; a 3 proton multiplet at 6.90 ppm; and a 1 proton triplet at 7.3 ppm.

B. Preparation of d,1-m-(mercaptoethylamidomethoxy)methamphetamine

To d,1-m-(methyldithioethylamidomethoxy)menthamphetamine (30 mg, 0.092 mmoles—from example A above) in 3.65 ml methanol (degassed with argon for 15 minutes) was added dithioerythritol (DTE, 13.5 mg, 0.0875 mmole) and triethylamine (13.9 µl) at room temperature under argon. After two hours, an aliquot was withdrawn and spotted on tlc (silica gel eluted with 1:4 parts by volume methanol:methylene chloride) which showed the formation of the title compound when sprayed using Ellman's reagent. The solvent was evaporated and an additional amount of methanol (1 ml—degassed with argon for 15 minutes) was added. The solvent was again evaporated and the resulting product dried under reduced pressure using a vacuum pump at room temperature for 1 hour to yield the title compound.

This compound was then stored under argon at 0°.

3. Preparation of d-p-(methyldithioethylamidomethyl)methamphetamine

A. Preparation of N-(2,2,2-trichloroethoxycarbonyl)-methamphetamine

D-methamphetamine hydrochloride (12 g, 0.064 moles) was dissolved in 70 ml of water in a 500 ml round bottom flask equipped with a stirring bar. To this solution was added sodium carbonate (13.5 g, 0128 moles). After the sodium carbonate was dissolved, tetrahydrofuran (70 ml) was added and then trichloroethylchloroformate (10.7 ml) was added dropwise. The reaction was vigorously stirred.

Afterwards, the system was made acidic to pH≈3 with concentrated HCl. The tetrahydrofuran was removed by concentrating on a rotary evaporator. The resulting aqueous solution was extracted with methylene chloride (3×100 ml) and the organic solutions combined, dried over anhydrous magnesium sulfate, filtered and concentrated to yield the title compound (20 g). NMR of this product in CDCl$_3$ shows a 3 proton doublet at 1.2 ppm; a 5 proton multiplet at 2.85 ppm; a 3 proton multiplet at 4.6 ppm; a 5 proton singlet at 7.2 ppm.

B. Preparation of N-(2,2,2-trichloroethoxycarbonyl)-p-(ethylcarboxycarbonyl)methamphetamine Into a 500 ml round bottom flask equipped with a stirrer and a calcium chloride drying tube was added N-(2,2,2-trichloroethoxycarbonyl)methamphetamine (17.0 g, 0.052 moles) and dried methylene chloride (300 ml). To this system was added ethyl oxalyl chloride (11.4 ml). The system was cooled in an ice bath to 0° and aluminum chloride (30 g, 5×6 g every 15 minutes) was added. When the addition was complete, the reaction was allowed to warm to ambient temperatures and stirred overnight. The reaction system was then added to 600 ml of water at about 0° and then sufficient sodium bicarbonate was added to the system to obtain a pH of about 8–9. The resulting solution was then filtered to remove solids and the organic phase isolated. The aqueous phase was again extracted with methylene chloride (200 ml) and the organic phases combined. The organic solution was then dried over anhydrous magnesium sulfate and concentrated to yield 15.9 g of the title compound.

C. Preparation of N-(2,2,2-trichloroethoxycarbonyl)-p-(carboxycarbonyl)methamphetamine To a solution of 1:1:0.5 methanol:tetrahydrofuran: 1N NaOH was added N-(2,2,2-trichloroethoxycarbonyl)-p-(ethylcarboxycarbonyl)methamphetamine (17 g). The system was then stirred for 16 hours. Afterwards, water (100 ml) was added to the system and the organic solvents removed via a rotary evaporator. The resulting aqueous solution was then extracted with ethyl acetate (2×50 ml) and then made acidic to pH=3.5 by addition of concentrated HCl. At this point the product began to precipitate. This precipitate was air dried to yield the title compound. NMR of this product in CDCl$_3$/CD$_3$OD shows a 3 proton doublet at 1.1 ppm; a 5 proton multiplet a 2.8 ppm; a 3 proton multiplet at 4.6 ppm; a 2 proton multiplet at 7.2 ppm; and a 2 proton doublet at 8.1 ppm.

D. Preparation of N-(2,2,2-trichloroethoxycarbonyl)-p-(carboxymethyl)methamphetamine Into a reaction vessel was added N-(2,2,2-trichloroethoxycarbonyl)-p-(carboxycarbonyl)methamphetamine (2.5 g), 10% palladium on carbon (1 g), glacial acetic acid (40 ml) and perchloric acid (1 ml). The vessel was degassed and purged with nitrogen (3 times) and then subjected to hydrogenolysis under 50 psi hydrogen for 20 hours. The reaction was then stopped and the reaction system filtered. The filtrate was concentrated on a rotary evaporator and then under vacuum. The resulting residue was purified on preparative thick layer chromatography plates (silica gel, eluted with 1:9 parts by volume methanol:methylene chloride). The desired band was washed (3:7 parts by volume methanol:methylene chloride) and concentrated to yield a product (1.9 g) which was further purified by thick layer chromatography (silica gel, eluted with 1.5:100 parts by volume acetic acid to a 7:3 parts by volume ethyl acetate:hexane). The desired band was washed, concentrated, dried to yield the title product (1.8 g).

E. Preparation of N-(2,2,2-trichloroethoxycarbonyl)-p-(methyldithioethylamidomethyl)methamphetamine N-(2,2,2-trichloroethoxycarbonyl)-p-(carboxymethyl)methamphetamine (1.25 g) was combined in dry methylene chloride (25 ml) with N,N-dicyclohexylcarbodiimide (0.865 g) and N-hydroxysuccinimide (0.483 g). A precipitate formed almost immediately and the reaction was allowed to continue for six hours at ambient temperature. At this time, this solution was added dropwise to a stirring solution of methyldithioethylamine hydrochloride (1.08 g) and triethylamine (1.06 g) in methylene chloride (25 ml). The reaction was continued overnight and then the solution was filtered and the filtrate washed with water (2×50 ml). The organic solution was then dried over anhydrous magnesium sulfate and concentrated. The product was purified by thick layer chromatography (silica gel, eluted with 1:1 parts by volume ethyl acetate:hexane). The desired band was isolated, washed and the resulting solution concentrated to yield the title product (1.4 g).

F. Preparation of p-(methyldithioethylamidomethyl)methamphetamine

To a 10% solution of acetic acid (25 ml) was added N-(2,2,2-trichloroethoxycarbonyl)-p-(methyldithioethylamidomethyl)methamphetamine (750 mg) and metallic zinc (975 mg). The reaction was maintained at room temperature for 16 hours and then the system was filtered and the resulting solution concentrated. To the resulting residue was added water (20 ml) and tetrahydrofuran (20 ml). This solution was then added dropwise to methyl methane thiosulfonate (680 mg) and the resulting system stirred overnight. The system was then treated to remove the organic solvent portion and the resulting aqueous solution was made basic with sodium carbonate and extracted with methylene chloride (4×30 ml) to yield a crude residue (325 mg). This residue was purified by thick layer chromatography (alumina, eluted with 1:9 parts by volume methanol:methylene chloride). The desired band was isolated and washed with 2:8 methanol:methylene chloride. The resulting solution was concentrated to dryness and then further dried under vacuum to yield the title compound (300 mg). NMR of this product in CDCl$_3$ shows a 3 proton doublet at 1.09 ppm; a 1 proton singlet at 1.35 ppm; a 3 proton singlet at 2.37 ppm; a 3 proton singlet at 2.42 ppm; a 5 proton multiplet at 2.81 ppm; a 4 proton multiplet at 3.6 ppm; a 1 proton broad peak at 6.09 ppm; and a 4 proton singlet at 7.2 ppm.

In a manner similar to that set forth in steps A through F above, d-p-methyldithioethylamidomethyl amphetamine was also prepared.

4. Preparation of m-(β-mercaptoethylthio)methamphetamine

A. Preparation of m-nitrophenyl acetone

A mixture of 3-nitrophenyl acetic acid (20 g), pyridine (44 g) and acetic anhydride (106 g) was refluxed for four hours. Complete disappearance of starting material was observed by tlc (silica gel eluted with 1:1 parts by volume diethyl ether:hexane), and the brown solution was then evaporated to dryness in vacuo at 40°. The resulting residue was refluxed in the presence of concentrated HCl (7.5 ml) and ethanol (78 ml) for one hour; and to the hydrolysis product was added ice water (400 ml) and the precipitating 3-nitrophenyl acetone was filtered and washed with water. Additional product was obtained by extracting the filtrate with methylene chloride, drying over sodium sulfate, and evaporating the organic solvents. The crude products were combined and dissolved in a minimum amount of methanol:methylene chloride (1:1 parts by volume). Silica gel (30–50 g, flash chromatography, EM 230–400 mesh) was added and the solvent evaporated. The dried silica gel was placed on a column (3 in.×6 in.) containing the same silica gel and eluted with 4:6 parts by volume ethyl acetate:hexane. The solution containing the desired product was evaporated to give the title compound. NMR for this product (in CDCl$_3$) shows a 3 proton singlet at 2.34 ppm; a 2 proton singlet at 3.63 ppm; a 2 proton multiplet at 7.5 ppm; and a 2 proton multiplet at 8.0 ppm.

B. Preparation of d,1 m-nitromethamphetamine

To m-nitrophenyl acetone (8.4 g—prepared in Step A above) in a mixture of 200 ml of isopropanol and 180 ml of tetrahydrofuran was added under nitrogen at room temperature a solution of methylamine hydrochloride (10.4 g) in 100 ml of water. To the resulting solution were then added sodium acetate (7.2 g) and sodium cyanoborohydride (2.9 g) and the pH of the mixture was adjusted to 7. After 18 hours, the reaction was found to be incomplete; and more reagents, methylamine hydrochloride (5.2 g) and sodium cyanoborohydride (1.5 g), were added. The mixture was allowed to stir overnight and then the organic solvents evaporated. The product was dissolved in 2% HCl solution (about 50 ml) and the pH adjusted to 2. The aqueous solution was extracted with hexane-ether (1:1 parts by volume) and then ether and the aqueous solution was extracted with methylene chloride. The organic solution was dried over sodium sulfate and evaporated to yield the title compound. This product was purified by dissolving it in a minimum amount of methylene chloride:methanol to which was added silica gel (flash chromatography). The mixture was evaporated to dryness and the residue placed on a column (3 in.×6 in.) of silica gel (flash chromatography, EM 230–400 mesh). The column was successively eluted with methylene chloride, 1:19 parts by volume methanol:methylene chloride, 1:9 parts by volume methanol:methylene chloride, and 1:4 parts by volume methanol:methylene chloride. Fractions of the desired product were collected and evaporated to yield 3.6 g of the title product. NMR for this product (in $CDCl_3$) shows a 3 proton doublet at 1.05 ppm; a 1 proton singlet at 2.08 ppm; a 3 proton singlet at 2.43 ppm; a 3 proton multiplet at 2.85 ppm; a 2 proton multiplet at 7.5 ppm and a 2 proton multiplet at 8.0 ppm.

C. Preparation of d,1-m-aminomethamphetamine

To m-nitromethamphetamine (3.5 g) dissolved in a mixture of methanol (68 ml) and tetrahydrofuran (68 ml) were added powdered sodium dithionite (21.9 g) and phosphate buffer (pH 7, 175 ml). The cloudy reaction mixture was allowed to stir at room temperature for 1 hour, and complete reaction was observed on tlc (silica gel eluted with 1:4 parts by volume methanol:-methylene chloride).

The product was then evaporated to dryness and the residue was added to methanol (about 50 ml) and the pH was adjusted to 9 using 1N NaOH. The inorganic salts were filtered off, and the filtrate was evaporated to dryness. The residue was again treated with methanol and the inorganic salts filtered off. The residue thus obtained was dissolved in a minimum amount of 1:1 parts by volume water:methanol and mixed with silica gel (about 10 g, flash chromatography). The silica gel suspension was evaporated to dryness and placed on a column (3 in.×6 in.) containing silica gel (flash chromatography, EM 230–400 mesh). The column was then eluted successively with 3:97 parts by volume methanol:methylene chloride (200 ml); 1:9 parts by volume methanol:methylene chloride (500 ml); 1:4 parts by volume methanol:methylene chloride until the desired product was eluted off the column. Fractions of the desired product were collected and the solvent evaporated to yield 3.6 g of the desired product.

In this reaction, all solvents were degassed with nitrogen for at least 15 minutes before use.

D. Preparation of d,1-m-(methyldithioethylthio)methamphetamine

To d,1-m-aminomethamphetamine (211 mg, 1.3 mmoles) dissolve in a mixture of concentrated sulfuric acid (0.306 ml) and water (20 ml) was added a solution of sodium nitrite (89 mg, 1.29 mmoles) in water (1.14 ml) at −5° to 0° for a period of one hour. After an additional one-half hour, complete reaction was observed by the tlc of an aliquot of the reaction mixture, which was basified before being spotted on the tlc.

To the resulting diazonium salt was added 1,2-dithioethane (539 μl) and the pH was adjusted to 8.5 using 10% NaOH at room temperature. After 10 minutes, a small aliquot was withdrawn and added to a solution of ethyl acetate and 5% aqueous solution of sodium bicarbonate. The tlc of the ethyl acetate layer (silica gel eluted with 1:4 parts by volume methanol:methylene chloride) showed a new spot which turned yellow when Ellman's spraying reagent was used and purple-brown when Ninhydrin spray was used. After twenty minutes at room temperature, methylmethanethiosulfonate (1.3 ml) in 116 ml of methanol (degassed by bubbling with nitrogen) was added; and the reaction mixture was allowed to stir at room temperature for two hours. The pH of the solution was adjusted to 3 and extracted with ether to remove nonbasic thiol compound. The pH of the aqueous solution was adjusted to 8.5, and the solution was extracted with methylene chloride and dried over sodium sulfate. The organic layer was evaporated and the crude product purified by preparative thick layer chromatography (silica gel eluted with 1:4 methanol:methylene chloride). The desired band was collected and washed to yield the title compound (10 mg). NMR for this product (in $CDCl_3$-$D_2O$) shows a 3 proton doublet at 1.2 ppm; a 3 proton singlet at 2.4 ppm; a 3 proton singlet at 2.67 ppm; a 7 proton multiplet from 2.5–3.4 ppm; and a 4 proton multiplet at 7.4 ppm.

E. Preparation of d,1-m-(β-mercaptoethylthio)methamphetamine

To d,1-m-(methyldithioethylthio) methamphetamine (14 mg, 0.049 mmoles—prepared in a manner similar to steps A–D of this Example 4) dissolved in methanol (1 ml) were added dithioerythritol (7.1 mg, 0.046 mmoles) and triethylamine (6.8 μl) under nitrogen at room temperature. After two hours, the formation of the mercapto product was observed on tlc (silica gel eluted with 1:4 parts by volume methanol:methylene chloride). The solution was then evaporated at room temperature and reduced pressure to yield the title compound.

In this example, all solvents employed were first degassed with nitrogen.

5. Preparation of d,1-m-(β-mercaptoethoxy)amphetamine

A. Preparation of methyldithioethyl chloride

A solution of methyl methanethiol sulfonate (6 g, 0.0396 mole) in 10 ml of methanol (degassed by bubbling with nitrogen for at least 10 minutes) is added dropwise to a solution of 2-chloroethanethiol (3.8 g, 0.0396 mole) in 10 ml of methanol (also degassed by bubbling with nitrogen for at least 10 minutes). After addition, the resulting solution is allowed to stir at room temperature until the reaction is complete. The solution is then evaporated and the title product is purified by chromatography.

B. Preparation of m-(methyldithioethoxy)phenyl acetone

To m-hydroxyphenyl acetone (3.0 g, prepared as in Step A of Example 1) in 200 ml of N,N-dimethylformamide under nitrogen is added potassium carbonate (0.46 g) at 0°. After addition, the system is allowed to come to room temperature. At this point, methyldithioethyl chloride (2.84 g) dissolved in 10 ml of N,N-dimethylformamide is added dropwise to the system. After complete addition of the methyldithioethyl chloride, the reaction is stirred at room temperature until the reaction is complete. At this point, the solvent is evaporated and the residue is purified by column chromatography to yield the title compound.

C. Preparation of d,1-m-(methyldithioethoxy)amphetamine

To a solution of m-(methyldithioethoxy) phenyl acetone, (2.2 g, 0.01 mole) in methanol (70 ml, degassed by bubbling with nitrogen for 15 minutes) is added ammonium acetate (3.85 g, 0.05 mole) at room temperature under nitrogen. After half an hour, sodium cyanoborohydride (724.5 mg, 0.0115 mole) is added into the system under nitrogen. After the reaction is complete, glacial acetic acid is slowly added to adjust the pH of the system to about 4.5. The resulting product is concentrated using a rotary evaporator to remove methanol and to the solution thus obtained is added sodium chloride (3.3 g) and water (16 ml). The resulting solution is then extracted using methylene chloride and the resulting methylene chloride solution is dried over sodium sulfate. The solution is then evaporated and the residue is purified by chromatography to yield the title compound.

D. Preparation of d,1-m-($\beta$-mercaptoethoxy) amphetamine

To d,1-m-(methyldithioethoxy) amphetamine (25.7 mg, 0.1 mmole) in 0.7 ml of methanol (degassed with argon) is added dithioerythritol (DTE, 15.4 mg, 0.1 mmole) in 1 ml of methanol (degassed with argon) and then triethylamine (13.3 $\mu$l) under argon. The system is stirred until the reaction is complete and then the solvent is evaporated. The residue is dissolved in methanol (1.3 ml—degassed with argon) and the solvent is again evaporated. The resulting product is then dried under reduced pressure using a vacuum pump at room temperature to yield the title compound.

6. Preparation of d,1-p-(carboxymethoxy)-N-trifluoroacetyl methamphetamine

A. Preparation of d,1-p-(methylcarboxymethoxy)-N-trifluoroacetyl amphetamine

A mixture of N-trifluoroacetyl-p-hydroxyamphetamine (0.5 g, prepared by reacting p-hydroxyamphetamine as either the free base or the hydrogen bromide salt with trifluoroacetic anhydride), anhydrous potassium carbonate (1.5 g), methyl chloroacetate (1 ml) and dry acetone (30 ml) was refluxed overnight with the exclusion of moisture. The cooled reaction mixture was filtered and the filtrate evaporated to give a crystalline mass. Recrystallization from chloroformhexane gave long needles of the title compound (555 mg). NMR of this product in $CDCl_3$ showed a 3 proton doublet at 1.3 ppm; a 2 proton doublet at 2.8 ppm; a 3 proton singlet at 3.9 ppm; a 2 proton singlet at 4.7 ppm; a 1 proton broad peak centered at 6.4 ppm; and a 4 proton doublet of doublets at 7.0 ppm.

B. Preparation of d,1-p-(methylcarboxymethoxy)-N-trifluoroacetyl methamphetamine To a refluxing mixture of p-(methylcarboxymethoxy)-N-trifluoroacetyl amphetamine (160 mg, 0.5 mmole) and methyl iodide (285 mg, 2 mmoles) in dry acetone (5 ml) was added potassium hydroxide (112 mg, 2 mmoles). The heating was continued for 8 minutes. Acetic acid (2 ml) was added to the cooled (ice) reaction mixture and the solvent evaporated to dryness. The residue was purified by preparative thick layer chromatography (silica eluted with ether) to yield 95 mg of the title compound. NMR of this product showed a 3 proton doublet at 1.3 ppm; a 5 proton multiplet at 3.0 ppm; a 3 proton singlet at 3.9 ppm; a 2 proton singlet at 4.7 ppm; and a 4 proton multiplet at 7.1 ppm.

C. Preparation of d,1-p-(carboxymethoxy)-N-trifluoroacetyl methamphetamine

Crude p-(methylcarboxymethoxy)-N-trifluoroacetyl methamphetamine ($\sim$1 g) was mixed with 1N NaOH (30 ml) and the mixture was kept at 80° C. for one hour. The solvent was evaporated and the brown residue was taken up in 2N HCl and the clear solution evaporated to dryness. The well-dried ($P_2O_5$) residue was extracted with boiling iso-propanol (2$\times$50 ml) and the brown solution treated with Norit and filtered. Evaporation of the solvent left a light brown oil which was mixed with trifluoroacetic anhydride (20 ml) and the mixture was refluxed for one hour. Evaporation of the solvent left a gummy residue which was treated with boiling water and then extracted with ether. The ether was dried and evaporated to yield the title product (600 mg). NMR of this product in $CDCl_3$ showed a 3 proton doublet at 1.2 ppm; a 5 proton multiplet at 2.8 ppm; a 2 proton singlet at 4.6 ppm; a 4 proton multiplet at 7.0 ppm; and a 1 proton singlet at >8.0 ppm.

CONJUGATES

7. Conjugation of d,1-m-(mercaptoethylamidomethoxy)amphetamine to KLH

A. Preparation of bromoacetic acid N-hydroxysuccinimic ester

To a solution of bromoacetic acid (10 g, 0.072 mole) in 255 ml of dry tetrahydrofuran (dried over molecular sieves 3Å) was added N-hydroxysuccinimide (8.28 g, 0.072 mole) and dicyclohexylcarbodiimide (14.9 g, 0.072 mole) and the resulting white suspension was allowed to stir at room temperature overnight. The white precipitates were filtered off, and the filtrate was then evaporated to dryness to yield crude bromoacetic acid N-hydroxysuccinimic ester. The resulting bromoacetic acid N-hydroxysuccinimic ester was then dissolved in a minimum amount of methylene chloride at room temperature, and hexane was added until cloudiness occurred. The resulting product was cooled at 5° C. overnight to yield recrystallized bromoacetic acid N-hydroxysuccinimic ester (12 g).

B. Preparation of bromoacetyl KLH

A suspension of KLH (618 mg) in phosphate buffer (0.1M, pH 8.5, 0.1M sodium chloride, 60 ml) was allowed to stir at 5° C. for 2 hours. To the cloudy mixture was added sufficient 1N NaOH solution to adjust the pH of the system to 10. The resulting system was allowed to stir at 5° C. overnight and then centrifuged at 8000 rotations per minute (rpm) at 4° C. for 10 minutes. The supernatant was decanted and the pH of this solution was adjusted to 8.5 using 1N HCl. To this solution was added bromoacetic acid N-hydroxysuccinimic ester (267 mg—prepared in step A of this Example 6) dissolved in N,N-dimethylformamide (3 ml) at 5° C. for a period of 30 minutes while maintaining the pH at 8. The resulting conjugate was stirred at 5° C. for 18 hours. Afterward, the solution was concentrated to 30 ml using Diaflo ® ultrafiltration membrane (PM 10, 43 mm—available from Amicon Corporation, Scientific Systems Division, Danvers, Mass.) and then passed through Sephadex G50 (eluted using 0.1M phosphate buffer, pH 7.5). The protein fractions were pooled to yield a solution of the title product.

C. Conjugation of d,1-m-(mercaptoethylamidomethoxy)amphetamine to KLH

To d,1-m-(methyldithioethylamidomethoxy)amphetamine (41.4 mg, 0.132 mmole—prepared in step F of Example 1) in methanol (5 ml) was added a solution of dithioerythritol (20 mg, 0.130 mmole) in methanol (127 μl) and then triethylamine (19.3 μl) under argon. The resulting solution was then allowed to stir at room temperature for 2 hours. The solvent was then evaporated to dryness, then an additional amount of methanol was added. The solvent was again evaporated and the resulting product was then dried under reduced pressure using a vacuum pump at room temperature to yield d,1-m-(mercaptoethylamidomethoxy)amphetamine as an oily product. This product was then dissolved in N,N-dimethylformamide and then added to the entire bromoacetyl KLH solution prepared in Step B of this Example 7. After 72 hours, the resulting conjugate was then concentrated using Diaflo® ultrafiltration membrane (PM 10, 43 mm) to 30 ml and then passed through Sephadex G50 (eluted using phosphate buffer, 0.1M, pH 7.5, 0.1M sodium chloride). The protein fractions were pooled and dialyzed using water-ammonia ($3 \times 2$ liters) and lyophilized to yield 402 mg of KLH conjugate of d,1-m-(thioethylamidomethoxy)amphetamine having a hapten number of 1024. (All solvents employed in this step C were degassed by bubbling with argon for 15 minutes before use.)

The hapten number of KLH conjugate of d,1-m-(thioethylamidomethoxy)amphetamine was calculated by comparing the UV absorbance with a mechanical mixture of d,1-m-(methyldithioethylamidomethoxy)amphetamine and unconjugated KLH in 0.01N NaOH at $\lambda=276$ nm.

8. Conjugate of d,1-m-(mercaptoethylamidomethoxy)methamphetamine to KLH

A. Preparation of bromoacetyl acid KLH

A solution of bromoacetyl N-hydroxysuccinimic ester (200 mg, prepared in step A of Example 7) in 2.25 ml of dry N,N-dimethylformamide was added to KLH (463 mg) in 45 ml of buffer (0.1M phosphate, pH 8.5, 0.1M sodium chloride) for a period of 40 minutes at pH 8 and at 5°. The resulting solution was allowed to stir overnight at 5° and then passed through Sephadex G50 (eluted using 0.1M phosphate buffer, pH 7.5, 0.1M sodium chloride). The protein fractions were pooled to yield a solution of the title compound.

B. Conjugation of d,1-m-(mercaptoethylamidomethoxy)methamphetamine to KLH

To the bromoacetyl KLH prepared in step A above was added d,1-m-(mercaptoethylamidomethoxy)methamphetamine (prepared in step B of Example 2) in 2 ml of N,N-dimethylformamide. The resulting conjugate was then concentrated to 30 ml using Diaflo® ultrafiltration membrane (PM 10, 43 mm) and then passed through Sephadex G25 (eluted using 0.1M phosphate buffer, pH 8) and then dialyzed against aqueous ammonium hydroxide (pH 8). The conjugate was then lyophilized to yield 268 mg of KLH conjugate of d,1-m-(mercaptoethylamidomethoxy)methamphetamine having a hapten number of 612.

The hapten number of the KLH conjugate of d,1-m-(mercaptoethylamidomethoxy)methamphetamine was calculated by comparing the UV absorbance with a mechanical mixture of the unconjugated KLH, and d,1-m-(methyldithioethylamidomethoxy)methamphetamine in 0.1N NaOH at $\lambda=276$ nm.

9. Conjugation of d-p-(mercaptoethylamidomethyl)-methamphetamine to bromoacetylglycine KLH A. Preparation of bromoacetylglycine-KLH To KLH (1 g, 60.5%) in 0.1M sodium carbonate and sodium bicarbonate at pH=8.5 was added dropwise a solution of bromoacetylglycine N-hydroxysuccinimic ester (prepared by reacting 0.121 g bromoacetylglycine, 0.150 g dicyclohexylcarbodiimide, and 0.084 g N-hydroxysuccinimide in 5 ml N,N-dimethylformamide overnight at room temperature and then filtering the solution through glass wool into the KLH solution). The addition was monitored with a pH meter and the pH was adjusted as necessary to maintain the pH between 8-8.5. After addition was complete, the pH was maintained at pH 8 for 20 minutes and then adjusted to pH 7 by addition of 0.1N HCl. The resulting product was passed through Sephadex G50 (eluted with distilled water) and the protein fractions pooled to yield a solution of the title compound.

B. Conjugation of d-p-(mercaptoethylamidomethyl)-methamphetamine to bromoacetylglycine KLH i) Preparation of d-p-(mercaptoethylamidomethyl)-methamphetamine d-p-(methyldithioethylamidomethyl)methamphetamine (23.7 mg) was combined with dithioerythritol (10.5 mg) in methanol (2.5 ml degassed by vacuum and the purged with argon-5 times). At this time, triethylamine (5 μl) was added. The reaction continued for 2 hours and tlc indicated reaction completion (sprayed with Ellman's reagent yield a yellow spot). The solution was concentrated and the residue placed under high vacuum for 3 hours to yield d-p-(mercaptoethylamidomethyl)methamphetamine.

ii) Conjugation

The entire d-p-(mercaptoethylamidomethyl)methamphetamine prepared in i) above was dissolved in N,N-dimethylformamide (2 ml, degassed with argon) and the resulting solution added dropwise to a solution of bromoacetylglycine-KLH (25 ml, prepared by taking the sufficient amount of the bromoacetylglycine KLH solution prepared in step A above to provide 200 mg conjugate (15 ml) and adding to this solution 10 ml of 0.2M phosphate buffer and then degassing the resulting solution with argon). The pH was maintained at between 7.0-7.2 by addition as required of 0.1N HCl. Afterwards, the system was filtered through Sephadex G50 (eluted with distilled water, pH 7). The protein fractions were pooled and then lyophilized to yield the conjugate of d-p-(mercaptoethylamidomethyl)methamphetamine to bromoacetylglycine-KLH which had a hapten number of 186.

The hapten number of this conjugate was determined by reacting the conjugate of bromoacetylglycine-KLH with Ellman's reagent and then comparing the UV absorbance of the resulting compound against free KLH which indicated that 186 bromoacetylglycines were attached to the KLH. Because the d-p-(mercaptomethylamidomethyl)methamphetamine was used in substantial excess over the bromoacetylglycine-KLH in the above conjugation reaction, it is assumed that all of the bromo groups on the bromoacetylglycine-KLH conjugate will react with d-p-(mercaptoethylamidomethyl)methamphetamine and accordingly the hapten number for the resulting product will be the same as the hapten number for the bromoacetylglycine-KLH.

10. Conjugation of d,1-m-(β-mercaptoethylthio)methamphetamine to KLH

To bromoacetyl KLH (prepared according to step A of Example 8) in a solution of N,N-dimethylformamide (10 ml) and phosphate buffer (45 ml, 0.05M, pH 7) was added d,1-m-(β-mercaptoethylthio)methamphetamine (prepared in step E of Example 4) at 0°-5° C. and the system was stirred overnight at 5° C. Then to the conjugate was added mercaptoethanol (35 μl) and the system was allowed to stand at room temperature for one hour. The resulting conjugate was passed through Sephadex G25 (eluted an aqueous solution of ammonium hydroxide, (pH 8.5). The protein fractions were pooled and dialyzed against 5 times 4 liters of water (NH$_4$OH, pH 8) and lyophilized to yield 46.6 mg of the title product having a hapten number of 494.

The hapten number of the KLH conjugate of d,1-m-($\beta$-mercaptoethylthio)methamphetamine was determined by comparing the UV absorbance with a mechanical mixture of d,1-m-(methyldithioethylthio)methamphetamine and unconjugated KLH in 0.05N NaOH at $\lambda=282$ nm.

11. Conjugation of d,1-p-(carboxymethoxy)methamphetamine to BSA

To a solution of the d,1-p-(carboxymethoxy)-N-trifluoroacetyl methamphetamine (350 mg, 1.1 mmoles) in dry N,N-dimethylformamide cooled in ice-salt bath ($\approx 10°$ C.), was added dry triethylamine and after stirring for two minutes, isobutyl chloroformate was added. The reaction mixture was stirred for 15 minutes at $-10°$ C. to $-6°$ C. and 15 minutes at $0°$ C. The mixed anhydride thus obtained was added to a fast-stirred solution of BSA (1 g) in a mixture of water, sodium bicarbonate and methanol which was cooled in ice. The clear solution was kept overnight at $0°$ C. Piperidine was added and the mixture was stirred at $0°$ C. for 2 hours (this removes the trifluoroacetyl protecting group). The conjugate was purified by dialysis (4 days). The yield of the title compound was 700 mg having a hapten number of 9.

The hapten number of the BSA conjugate of d,1-p-(carboxymethoxy)methamphetamine was determined by comparing the UV absorbance with a mechanical mixture of d,1-p-(carboxymethoxy)methamphetamine, and unconjugated BSA in 0.1N NAOH at $\lambda=290$ nm.

12. Conjugation of d,1-m-(mercaptoethylamidomethoxy)amphetamine to G6PDH

A. Pretreatment of G6PDH Ammonium Sulfate Suspension

G6PDH ammonium sulfate suspension (20 ml, 9.98 mg/ml) was centrifuged at 10,000 rpm (Sorvall RC-5B) for 20 minutes. The supernatant was removed and the residual enzyme was dissolved in 20 ml of buffer (1% RSA and 0.9% sodium chloride in a buffer solution containing 0.055M Tris, 0.005% thimerosol and 0.5% NaN$_3$ at pH 8—hereinafter "Buffer A"). This solution was then dialyzed against three changes of Buffer A (4.0 liter each). The final volume of the enzyme preparation was 45 ml at a concentration of 3.7 mg/ml.

B. Conjugation of G6PDH to bromoacetic acid N-hydroxysuccinimic ester to form bromoacetyl-G6PDH To G6PDH (166 mg) in 45 ml of Buffer A was added G6P-disodium salt (1800 mg) and NADH (1800 mg) at $4°$ C. The pH of the solution was adjusted to 8.02. A 10 $\mu$l aliquot was then withdrawn and the enzyme activity was determined. Bromoacetic acid N-hydroxysuccinimic ester (130 mg, prepared in Step A of Example 7) was dissolved in 2.62 ml of dry N,N-dimethylformamide. Using a 100 $\mu$l Hamilton syringe, aliquots of bromoacetic acid N-hydroxysuccinimic ester were added to the solution and enzyme activity was determined after each addition. 77% of the enzyme was deactivated by addition of a total amount of 45 mg of bromoacetic acid N-hydroxysuccinimic ester and the conjugation procedure terminated. The product was then dialyzed against two changes of degassed, argon purged Buffer A (4.0 liter) to yield a solution of the title compound. The dialysis did not result in the loss of enzyme activity when volume is corrected.

C. Conjugation of the d,1-m-(mercaptoethylamidomethoxy)amphetamine to bromoacetyl-G6PDH All solutions used in the following reaction were first purged with argon. A solution of dithioerythritol (0.433 mmole) and triethylamine (60 $\mu$l) in 1.0 ml methanol was added to d,1-m-(methyldithioethylamidomethoxy)amphetamine (135 mg, 0.433 mmole-prepared in Step F of Example 1) in methanol (1.0 ml) under argon. The system was maintained at room temperature for 2 hours. Then an aliquot was withdrawn and spotted on tlc (silica gel eluted with 1:4 methanol:methylene chloride). It showed the formation of the sulfhydryl compound when tlc plate was sprayed using Ellman's reagent (yellow spot). The solvent was evaporated to dryness and an additional amount of methanol (1 ml) was added, and the solvent was evaporated again. The resulting product was dried under reduced pressure using a vacuum pump at room temperature for one hour. The resulting d,1-m-(mercaptoethylamidomethyl)amphetamine was dissolved in N,N-dimethylformamide (degassed, dry, 0.5 ml) which was added to the solution of the bromoacetyl-G6PDH (purged with argon, prepared in Step B of this Example 12) and the system reacted overnight at $4°$. A Sephedex G-25 column (5$\times$60 cm, bed volume 300 ml) was equilibrated with 1000 ml of Buffer A. The reaction system was applied to the column and the protein fractions pooled. The pooled fractions were dialyzed against three changes of Buffer A (6.0 liter each) to yield a solution of the title conjugate. This conjugate had an 81% inhibition of the enzyme when combined with anti-amphetamine monoclonal antibody, 26H8-AMPH.

13. Conjugation of d,1-m-(mercaptoethylamidomethoxy)methamphetamine to G6PDH

A. Pretreatment of G6PDH Ammonium Sulfate Suspension

G6PDH ammonium sulfate suspension (20 ml, 9.98 mg/ml) was centrifuged at 10,000 rpm (Sorvall RC-5B) for 20 minutes. The supernatant was removed and the residual enzyme was dissolved in 20 ml of Buffer A. This solution was dialyzed against three changes of Buffer A (4.0 liter each). The final volume of the enzyme preparation was 45 ml at a concentration of 3.7 mg/ml.

B. Conjugation of G6PDH to bromoacetic acid N-hydroxysuccinimic ester to form bromoacetyl-G6PDH To G6PDH (200 mg) in 40 ml of Buffer A was added G6p-disodium salt (1600 mg) and NADH (1800 mg) at $4°$. The pH of the solution was adjusted to 8.0. A 10 $\mu$l aliquot was then withdrawn and the enzyme activity was determined. Bromoacetic acid N-hydroxysuccinimic ester (50 mg, prepared in Step A of Example 7) was dissolved in 1.0 ml of dry N,N-dimethylformamide. Using a 100 $\mu$l Hamilton syringe, aliquots of bromoacetic acid N-hydroxysuccinimic ester were added to the solution and enzyme activity was determined after each addition. 66% of the enzyme was deactivated by addition of a total amount of 30 mg of bromoacetic acid N-hydroxysuccinimic ester and the conjugation procedure terminated. The product was then dialyzed against two changes of degassed, argon purged Buffer A (4.0 liter). The dialysis did not result in the loss of enzyme activity when volume is corrected.

C. Conjugation of the d,1-m-(mercaptoethylamidomethoxy)methamphetamine to bromoacetyl-G6PDH All solutions employed in this reaction were first purged with argon. A solution of dithioerythritol (0.354 mmole) and triethylamine (57 μl) in 1.0 ml methanol was added to d,1-m-(methyldithioethylamidomethoxy)-methamphetamine (120 mg, 0.368 mmole-prepared in Step A of Example 2) in methanol (1.0 ml) under argon. The system was maintained at room temperature for 2 hours. Then an aliquot was withdrawn and spotted on tlc (silica gel eluted with 1:4 methanol:methylene chloride). It showed the formation of the sulfhydryl compound when tlc plate was sprayed using Ellman's reagent (yellow spot). The solvent was evaporated to dryness and an additional amount of methanol (1 ml) was added, and the solvent was evaporated again. The resulting product was dried under reduced pressure using a vacuum pump at room temperature for one hour. The resulting d,1-m-(mercaptoethylamidomethoxy)methamphetamine was dissolved in N,N-dimethylformamide (degassed, dry, 1.0 ml) which was added to the solution of the bromoacetyl-G6PDH (purged with argon, prepared in Step B of this Example 13) and the system reacted overnight at 4°. A Sephedex G-25 column (5×60 cm, bed volume 300 ml) was equilibrated with 1000 ml of Buffer A. The reaction system was applied to the column and the protein fractions pooled. The pooled fractions were dialyzed against three changes of Buffer A (6.0 liter each) to yield a solution of the title conjugate. This conjugate had a 65% inhibition of the enzyme when combined with anti-methamphetamine monoclonal antibody, 10E12-METH.

14. Conjugation of d-p-mercaptoethylamidomethyl)-methamphetamine and d-p-(mercaptoethylamidomethyl)amphetamine to bromoacetylglycine-KLH In a manner similar to the procedures set forth in Examples 12 and 13 above, d-p-(mercaptoethylamidomethyl)methamphetamine and d-p-(mercaptoethylamidomethyl)amphetamine were conjugated to G6PDH. The amounts of reagents used in these procedures were as follows:

|  | Methamphetamine | Amphetamine |
|---|---|---|
| G6PDH | 5 mg | 5 mg |
| G6P-disodium salt | 40 mg | 40 mg |
| NADH | 40 mg | 40 mg |
| Bromoacetic acid N-hydroxysuccinimic ester | 5 mg | 6 mg |
| Dithioerythritol | 0.024 mmol | 0.021 mmol |
| Triethylamine | 0.023 mmol | 0.020 mmol |
| d-p-(methyldithioethylamidomethyl)methamphetamine | 7 mg | |
| d-p-(methyldithioethylamidomethyl)amphetamine | | 6 mg |
| bromoacetyl-G6PDH | 5 mg | 5 mg |

In the preparation of the methamphetamine derivatives, the conjugation with bromoacetic acid N-hydroxysuccinimic ester to form the bromoacetyl-G6PDH resulted in 62% enzyme deactivation; whereas in the preparation of the amphetamine derivatives, the conjugation with bromoacetic acid N-hydroxysuccinimic ester to form the bromoacetyl-G6PDH resulted in 83% enzyme deactivation. The conjugation to form the conjugate of d-p-(mercaptoethylamidomethyl)methamphetamine with G6PDH resulted in a conjugate having a 72% inhibition of the enzyme when combined with anti-methamphetamine monoclonal antibody, 10E12-METH; whereas the conjugation to form the conjugate of d-p-(mercaptoethylamidomethyl)methamphetamine with G6PDH resulted in a conjugate having a 70% inhibition of the enzyme when combined with anti-amphetamine monoclonal antibody, 26H8-AMPH.

ANTIBODIES

15. Preparation of Monoclonal Antibody for Amphetamine Designated 26H8

A. 5 mice (Balb/c) were immunized with two different immunogens, i.e., the conjugate of d,1-m-(mercaptoethylamidomethoxy)amphetamine to KLH ("Immunogen A"-prepared in Example 2 C above), and the conjugate of d,1-m-(β-mercaptoethylthio)methamphetamine to KLH ("Immunogen B"-prepared in Example 10 above) according to the following schedule:

| Immunization | Immunogen | Amount | Adjuvant | Delivery |
|---|---|---|---|---|
| Initial | Immunogen A | 200 μg | CFA | ip |
| Week 2 | Immunogen A | 200 μg | IFA | ip |
| Week 4 | Immunogen A | 200 μg | IFA | ip |
| Week 9 | Immunogen B | 150 μg | IFA | ip |
| Week 11 | Immunogen B | 150–200 μg | IFA | ip |
| Week 15 Day −3 | 1:1 mixture of | 200 μg | HBSS | iv |
| Day −2 | Immunogen A and | 400 μg | HBSS | iv |
| Day −1 | of Immunogen B | 400 μg | HBSS | iv |

B. At the end of this immunization schedule, the mice were sacrificed and the spleens removed and were ready for fusion to myeloma cells. The parental myeloma line used for all fusions was P3X63 Ag 8.653. Approximately $3-3.5 \times 10^7$ myeloma cells per spleen were spun down at 800 rpm for 8 minutes, then resuspended in 20 ml of DMEM. The excised spleens were cut into small pieces, gently crushed in a tissue homogenizer containing 7 ml DMEM, then added to the myeloma cells. The cell suspension was spun down at 800 rpm for 8 minutes and the supernatant poured off. The cells were resuspended in 2 ml/spleen 50% aqueous polyethylene glycol solution added over a 3-minute period with gentle swirling, then 1 ml/spleen DMEM was added over a 1.5-minute period, and 5 ml/spleen Super DMEM was added over an additional 1.5-minute period. The cells were spun down at 800 rpm for 8 minutes, the supernatant poured off, and the cells resuspended in HAT media, approximately 100 ml/spleen. The fusing cells were then plated out into four to six 96-well plates per spleen and placed in a CO₂ incubator. The plates were fed with HAT media on Day 7, with HT media on Day 10 and were screened on Day 12.

C. The primary fusion screen was a reverse ELISA procedure which was set up such that the monoclonal antibody is bound on the Enzyme Immunoassay (EIA) plate by rabbit anti-mouse Ig serum, and positive wells are selected by their ability to bind enzyme conjugates of the specific drug in question. The fusion was initially screened with both the conjugate of d,1-m-(mercaptoethylamidomethoxy)amphetamine to G6PDH (prepared in Example 12 C above-referred to in this Example as enzyme conjugate) and the conjugate of d,1-m-(mercaptoethylamidomethoxy)methamphetamine to G6PDH (prepared in Example 13C above-also referred to in this Example as enzyme conjugate). Positives from these primary screens were transferred to 24-well plates, allowed to grow for several days, then were screened by a competition reverse ELISA, wherein the enzyme conjugate must compete with free drug i.e., amphetamine, methamphetamine and drugs such as phenylpropanolamine, pseudoephedrine, ephedrine, etc, for antibody binding sites. If the enzyme activity measured when free drug was present was less than that seen when only enzyme conjugate is present, then the antibody preferentially binds the free drug over the enzyme conjugated form. Screening duplicate plates involving several different free drug solutions gave an indication of relative preference for each of the drugs. Selected wells from the competition screen were cloned by serial dilution at least four times, with cloning plates screened by reverse ELISA; occasional competition reverse ELISAs were used to eliminate more monoclonal antibodies during the cloning process.

Positives from the primary screen were also tested on a Cobas Bio analyzer for inhibition of enzyme conjugate and cross-reactivity with various free drug solutions in the EMIT ® assay configuration. Selected monoclonal antibodies were again tested for modulation and cross-reactivity and eliminated from consideration.

D. All cells were cloned and grown in macrophage-conditioned media. This media was made by injecting 10 ml of Super DMEM into the peritoneal cavity of an euthanized mouse. Macrophage cells were losened by tapping the outside of the cavity, and the media was withdrawn and added to 200 ml of Super DMEM. The cells were allowed to grow in a $CO_2$ incubator for 3-4 days, then the media was filtered through a 0.22 μm filter to remove all cells. The supernatant was mixed with 350 ml of additional Super DMEM. This resultant "macrophage-conditioned" media was stored at 4°. It was used within one month. Cloned lines were frozen down and stored at −100° in 10% DMSO (in Super DMEM) and also injected into mice for ascites production.

E. Monoclonal antibody subclasses were determined using a variety of mouse monoclonal antibody isotyping kits, most frequently those by Southern Biotechnology and Zymed. All are ELISA based, and culture supernatant and manufacturer's instructions were followed.

F. Monoclonal antibodies to amphetamine produced by the above procedure are designated as follows: 1E7, 1G4, 2G4, 5F7, 5H11, 6D1, 8H10, 9A12, 13B6, 15F1, 23D2, 24A12, 26H8. The monoclonal antibody 26H8 is sometimes referred to 26H8-AMPH to designate that it is specific for amphetamine. The isotypes of these antibodies are μ; $Y_1$; $Y_1$; undetermined; $Y_1$; $Y_1$; $Y_1$; $Y_3$, κ; $Y_{2a}$; undetermined; $Y_{2a}$; $Y_1$ or A; and $Y_1$ respectively.

16. Preparation of Monoclonal Antibody for Methamphetamine Designated 10E12

A. 2 mice (Balb/c) were immunized with a conjugate of d,l-p-(carboxymethoxy)methamphetamine to BSA ("Immunogen C"-prepared in Example 11 above) according to the following schedule:

| Immunization | Immunogen | Amount | Adjuvant | Delivery |
| --- | --- | --- | --- | --- |
| Initial | Immunogen C | 150 μg | CFA | ip |
| Week 2 | Immunogen C | 200 μg | IFA | ip |
| Week 4 | Immunogen C | 200 μg | IFA | ip |
| Week 6 | Immunogen C | 100 μg | IFA | ip |
| Week 8 | Immunogen C | 100 μg | IFA | ip |
| Week 10 | Immunogen C | 100 μg | IFA | ip |
| Week 16 | | | | |
| Day −3 | Immunogen C | 200 μg | HBSS | sc & iv |
| Day −2 | Immunogen C | 800 μg | HBSS | sc & iv |
| Day −1 | Immunogen C | 500 μg | HBSS | sc & iv |

The procedure set forth in Steps B through D of Example 15 above were repeated with only the following changes:

In Step C, the fusion was initially screened with only the conjugate of a ligand analog of d,1-m-(mercaptoethylamidomethoxy)methamphetamine to G6PDH.

The monoclonal antibody to methamphetamine produced by the above procedure is designated 10E12 which is sometimes referred to 10E12-METH to designate that it is specific for methamphetamine. The isotype of this antibody is $Y_1$,κ.

17. Preparation of Monoclonal Antibody for Methamphetamine Designated 8G5

A. 2 mice (CB6F1) were immunized with a conjugate of d-p-(thioethylamidomethyl)methamphetamine to KLH ("Immunogen D"-prepared in Example 14 above) according to the following schedule:

| Immunization | Immunogen | Amount | Adjuvant | Delivery |
| --- | --- | --- | --- | --- |
| Initial | Immunogen D | 150 μg | CFA | ip |
| Week 2 | Immunogen D | 100 μg | IFA | ip |
| Week 4 | Immunogen D | 100 μg | IFA | ip |
| Week 8 | Immunogen D | | | |
| Day −3 | Immunogen D | 200 μg | HBSS | sc |
| Day −2 | Immunogen D | 400 μg | HBSS | sc |
| Day −1 | Immunogen D | 400 μg | HBSS | sc |

The procedures set forth in Steps B through of Example 15 above were repeated with only the following changes:

In Step C, the fusion was initially screened with only the conjugate of a ligand analog of d-p-(mercaptoethylamidomethyl)methamphetamine to G6PDH.

The monoclonal antibodies to methamphetamine produced by the above procedure are designated 6B6, 8C4 and 8G5 which are sometimes referred to as 6B6-METH, 8C4-METH and 8G5-METH to designate that these antibodies are specific to methamphetamine. The isotype of 8G5 is $Y_1$,κ. The isotypes of the other antibodies were not determined.

COMPOSITIONS AND METHODS

18. Immunoassay for Amphetamines in Urine Samples

An immunoassay for amphetamines which employed a composition of this invention, was conducted on samples spiked with known concentrations of either d-amphetamine or d-methamphetamine. In addition to the samples, this immunoassay employed two reagents, i.e., "Reagent A" and "Reagent B", which comprised the following:

Reagent A: An aqueous reagent solution having a pH of 5.2 which contained the following:

0.055M Tris;
0.5% sodium azide;
0.066M G6P;
0.005% thimersol;
0.04M NAD;
1% of Sol-U-Pro (a protein processed from pig skin having a molecular weight of 1500 daltons (available from DynaGel Inc., Calumet City, Ill. 60409)
14.4 μg (per 50 μl of Reagent A) of an anti-amphetamine monoclonal antibody designated 26H8-AMPH; and
2.7 μg (per 50 μl of Reagent A) of an anti-methamphetamine monoclonal antibody designated 10E12-METH.

Reagent B: An aqueous reagent solution having a pH of 8.01 which contained the following:
0.055M Tris;
0.5% sodium azide;
1% of Sol-U-Pro;
0.005% thimersol;
0.9% sodium chloride;
0.3 μg of the conjugate of d,1-m-(mercaptoethylamidomethyl)amphetamine to G6PDH ($R_{max}$=505); 0.3 μg of the conjugate of d,1-(mercaptoethylamidomethyl)methamphetamine to G6PDH ($R_{max}$=502).

$R_{max}$ represents the maximum optical density (signal) which the signal producing system can generate under the assay conditions. $R_{max}$ is determined by measuring the optical density produced by combining the specified amount of each conjugate with the specified amounts of the other components of the signal producing system in the absence of either monoclonal antibody. The $R_{max}$ of each conjugate is additive and therefore the total $R_{max}$ of solution B is 1007.

PROTOCOL 17.5 μl of each sample was first combined with 17.5 μl of Reagent A and then 17.5 μl of Reagent B. The resulting solution was then added to 262.5 μl of diluent (an aqueous solution prepared by adding 15 parts by volume distilled water to 1 part by volume of EMIT ® Drug Assay Buffer 6A128 available from Syva Company, 900 Arastradero Road, Palo Alto, Calif. 94303; hereinafter "Diluent A") and the system was then incubated for 15 seconds. At this time, the absorbance of the system was then measured and a subsequent absorbance measurement made 30 seconds later. The second result was subtracted from the first result and this difference was taken as the change in optical density for that particular solution. This result was then compared against the result obtained in the same way using a negative calibrator, i.e., a solution prepared as above but not containing any amphetamines, as well as a low (cut-off) calibrator, i.e., a sample containing either 300 ng of amphetamine or 1000 ng of methamphetamine. This assay was conducted at 32°. The above procedure can be conducted on automated instrumentation such Syva's ETS TM analyzer which is available from Syva Company, 900 Arastradero Road, Palo Alto, Calif. 94303. In the instant example, two different ETS TM analyzers were employed. Except as otherwise indicated, the first instrument conducted only a single assay for each sample whereas the second instrument conducted duplicate assays for each sample.

In this assay, if amphetamine or methamphetamine is present in the sample, that drug will compete with the conjugate of the corresponding ligand analog with the enzyme for binding to the respective monoclonal antibody and accordingly this increases the amount of unbound conjugate. This results in an increase in enzyme activity because unbound conjugate has a greater enzyme activity that bound conjugate.

In this particular assay, the change in enzyme activity for the test solution is reported as the change in optical density (absorbance) at a wavelength of 340 nm wherein the pathlength of light is 1 cm. The protocol for this assay stipulates that a positive result requires a change in optical density of at least 40 EMIT ® assay units. That is to say that if the change in optical density for a particular test solution is less than 40 EMIT ® assay units, then that solution is determined to be negative for amphetamines; whereas if the change in optical density for a particular test solution is equal or greater than 40 EMIT ® assay units, then that solution is determined to be positive for amphetamines. This corresponds to an amphetamine cut-off of 300 ng/ml or a methamphetamine cut-off of 1000 ng/ml.

The results of this test for d-amphetamine spiked samples are as follows (+ =positive result for the presence of amphetamines; — =negative result for the presence of amphetamines):

| Sample No. | Nominal Concentration | ETS Analyzer No. 1 | ETS Analyzer No 2 |
|---|---|---|---|
| 1. | 100 ng/ml | — | — |
| 2. | 600 ng/ml | + | + |
| 3. | 0 ng/ml | — | — |
| 4. | 1000 ng/ml | + | + |
| 5. | 200 ng/ml | — | — |
| 6. | 500 ng/ml | + | + |
| 7. | 800 ng/ml | + | + |
| 8. | 900 ng/ml | + | + |
| 9. | 2000 ng/ml | + | + |
| 10. | 150 ng/ml | — | — |

The results of this test for d-methamphetamine spiked samples are as follows (+ and — are as above).

| Sample No. | Nominal Concentration | ETS Analyzer No. 1 | ETS Analyzer No 2 |
|---|---|---|---|
| 11. | 2000 ng/ml | + | + |
| 12. | 1500 ng/ml | + | + |
| 13. | 1200 ng/ml | + | + |
| 14. | 500 ng/ml | — | — |
| 15. | 750 ng/ml | — | +/—* |
| 16. | 0 ng/ml | — | — |
| 17. | 1700 ng/ml | + | + |
| 18. | 300 ng/ml | — | — |
| 19. | 600 ng/ml | — | — |
| 20. | 850 ng/ml | +/—** | +/—* |

*Upon initial analysis, duplicates disagreed (one was positive and one was negative). Upon repeat analysis, the duplicates agreed as negative.
**A replicate for this sample was positive; three additional replicates were all negative.

The above results establish that the compositions of the instant invention are effective in assaying for amphetamines.

19. Specificity of the Immunoassay

An immunoassay employing similar reagents as set forth in Example 18 above, was used to determine specificity of this immunoassay with prescription and OTC drugs. This example determined what concentration of drug was required to produce a signal equal to the low (cut-off) calibrator. The samples were run on two instruments, i.e., Syva's AutoCarousel TM Analyser and Syva's ETS TM Analyzer (both of which are available from Syva Company, 900 Arastradero Road, Palo Alto, Calif. 94304). The AutoCarousel TM analyzer uses a similar protocol as the ETS TM analyzer except it employs a different dilution ratios of sample to Reagents A and B to Diluent A.

The results of these tests indicate the minimum concentration of drugs required to produce a signal equal to the low calibrator, i.e., a positive result for the presence of amphetamine. These results were compared against a prior art EMIT ® amphetamines assay which employed a polyclonal antibody and a single conjugate of an amphetamine ligand analog and glucose-6-phosphate dehydrogenase. The prior art EMIT ® immunoassay was conducted on only one analyzer, i.e., an AutoCarousel analyzer. The immunoassay according to this invention was designated as "Immunoassay A" whereas the prior art immunoassay (which employs a polyclonal antibody) is designated as "Immunoassay B"). The results are as follows:

| Compound | Immunoassay A Auto-Carousel ™ Analyzer (μg/ml) | Immunoassay A ETS ™ Analyzer (μg/ml) | Immunoassay B Auto-Carousel ™ Analyzer (μg/ml) |
|---|---|---|---|
| l-ephedrine | 70 | 70 | 3.7 |
| phentermine | 0.37 | 0.56 | 2.6 |
| phenmetrazine | 360 | 230 | 5 |
| phenylpropanolamine | 145 | 150 | 4 |
| nylidrin | >750 | >750 | 17 |
| isoxsuprine | >500 | >500 | 33 |
| mephentermine | 28 | 25 | 3.7 |
| MDA* | 0.58 | 0.68 | 12 |
| MDMA** | 2.3 | 1.35 | 5 |

*MDA = methylenedioxyamphetamine
**MDMA = methylenedioxymethamphetamine

The above data establishes that the immunoassay employing a method and composition according to this invention has greater specificity for amphetamines than for certain prescription and OTC drugs as compared to an immunoassay employing a method and composition according to the prior art. In particular, significantly improved results were obtained for l-ephedrine, phenylpropanolamine, phenmetrazine, nylidrin, isoxsuprine and mephentermine while showing less specificity for phentermine, MDA and MDMA. However in regard to MDA and MDMA, the specificity to these drugs is an improvement over prior art immunoassays insofar as these two drugs can be abused.

The compositions and methods of this invention were further tested to establish their improved specificity over prior art compositions and methods. In this regard, one hundred fifty (150) patient samples were obtained. 50 samples had sufficient concentrations of amphetamines so that a positive result was expected; 50 samples had no concentration of amphetamines or substances which in a prior art EMIT ® immunoassay gave positive results for amphetamines but which had no concentration of amphetamines (as used herein "Amphetamine Negative without Substance"), 50 samples had concentrations of substances which in a prior art EMIT ® immunoassay gave positive results for amphetamines but which had no concentration of amphetamines (as used herein "Amphetamine Negative with Substance") and correctly should give a negative result for amphetamines. The immunoassay employing methods and compositions of this invention (immunoassay "A") was compared to a prior art EMIT ® immunoassay which employed a polyclonal antibody and a single conjugate of an amphetamine analog with glucose-6-phosphate dehydrogenase (immunoassay "B"). Both immunoassays were conducted on a Cobas Bio analyzer. The percent of samples in each that was correctly identified was as follows:

| Immunoassay | Amphetamines Positive | Amphetamines Negative with Substance | Amphetamines Negative without Substance |
|---|---|---|---|
| A | 96 | 88 | 100 |
| B | 100 | 0 | 96 |

In another comparison, one hundred (100) patient samples were obtained and which were confirmed to be contaminated with amphetamines at a concentration such that a positive result was expected, or Amphetamine Negative with Substance or Amphetamine Negative without Substance. The sample population was as follows: 48 samples had a concentration of amphetamines such that a positive result was expected, 13 samples either had a concentration of amphetamines below that which a positive result was expected or were Amphetamine Negative without Substance, 39 samples were Amphetamine Negative with Substance. The immunoassay employing methods and compositions of this invention (immunoassay "A") was compared to the prior art EMIT ® immunoassay as above (immunoassay "B"). Both immunoassays were conducted on an ETS ™ analyzer. The percent of samples in each group that was correctly identified was:

| Immunoassay | Amphetamines Positive | Amphetamines Negative with Substance | Amphetamines Negative without Substance |
|---|---|---|---|
| A | 98.2 | 82 | 100 |
| B | 100 | 0 | 100 |

The above results establish that the compositions and methods of this invention have significantly improved specificity over the prior art methods and compositions.

What is claimed is:

1. A reagent system comprising (i) at least two conjugates, wherein in one conjugate an enzyme is bound to an amphetamine ligand analog and in the other conjugate said enzyme is bound to a methamphetamine ligand analog, (ii) an antibody to amphetamine, and (iii) an antibody to methamphetamine, wherein at least one of said antibodies is a monoclonal antibody and each of said antibodies is moderately cross-reactive with that conjugate which binds more strongly with the other antibody.

2. A reagent system according to claim 1 which further comprises any other necessary components of the signal producing system wherein said producing system is capable of producing a detectable signal wherein the amount of signal is related to the amount of amphetamines in the solution.

3. A reagent system according to claim 1 wherein both of said antibodies are monoclonal.

4. A method for the assay of amphetamines in a sample suspected of containing amphetamine and/or methamphetamine which comprises A) combining in aqueous medium (a) said sample; (b) two conjugates wherein in one conjugate an enzyme is conjugated to a ligand analogue of amphetamine and in the other conjugate said enzyme is conjugated to a ligand analogue of methamphetamine; and (c) an antibody to amphetamine and an antibody to methamphetamine wherein at least one of said antibodies is a monoclonal antibody and each of said antibodies is moderately cross-reactive with that conjugate which binds more strongly with the other antibody under conditions allowing said antibodies to bind to said conjugates;

B) with or without separating the bound or unbound conjugates from the medium obtained from step A, contacting the conjugates obtained from step A with any necessary components of a signal producing system wherein a signal is produced that is related to the presence of amphetamines in said sample; and C) determining the signal and correlating the signal to the presence of amphetamine and/or methamphetamine in the sample.

5. A method according to claim 4 wherein said enzyme is glucose-6-phosphate dehydrogenase.

6. A method according to claim 4 wherein neither bound nor unbound conjugates are separated from the medium in Step B.

7. A method according to claim 4 wherein either bound or unbound conjugates are separated from the medium in Step B.

8. A method according to claim 4 wherein both of said antibodies are monoclonal.

9. A kit for use in an assay for amphetamines in a sample suspected of containing amphetamine and/or methamphetamine which comprises the following components:

(a) two conjugates each comprised of an enzyme wherein in one conjugate enzyme is bound to an amphetamine ligand analogue and in the other conjugate enzyme is bound to a methamphetamine ligand analogue, and wherein said enzymes are derived from the same enzyme; and (b) an antibody to amphetamine and an antibody to methamphetamine wherein at least one of said antibodies is a monoclonal antibody and each of said antibodies is moderately cross-reactive with that conjugate which binds more strongly with the other antibody.

10. A kit as defined in claim 9 which further comprises any other necessary members of the signal producing system.

11. A kit as defined in claim 9 wherein both of said antibodies are monoclonal.

12. A kit as defined in claim 9 wherein said enzyme is glucose-6-phosphate dehydrogenase.

* * * * *